United States Patent [19]
Marcus

[11] Patent Number: 5,086,226
[45] Date of Patent: Feb. 4, 1992

[54] DEVICE FOR RADIO FREQUENCY POWERED GLOW DISCHARGE SPECTROMETRY WITH EXTERNAL SAMPLE MOUNT GEOMETRY

[75] Inventor: R. Kenneth Marcus, Clemson, S.C.

[73] Assignee: Clemson University, Clemson, S.C.

[21] Appl. No.: 591,544

[22] Filed: Oct. 1, 1990

Related U.S. Application Data

[63] Continuation-in-part of Ser. No. 359,157, May 31, 1989, Pat. No. 5,006,706.

[51] Int. Cl.$^5$ .............................................. H01J 49/04
[52] U.S. Cl. ..................................... 250/288; 250/281; 250/282; 250/423 R
[58] Field of Search ................... 250/288, 288 A, 281, 250/282, 423 R; 356/314, 316, 311; 315/111.21

[56] References Cited

U.S. PATENT DOCUMENTS

| | | | |
|---|---|---|---|
| 3,588,601 | 6/1971 | Yamasaki | 356/314 |
| 3,626,234 | 12/1971 | Grimm | 386/316 |
| 4,128,336 | 12/1978 | Butler | 356/314 |
| 4,853,539 | 8/1989 | Hall et al. | 250/288 |
| 4,912,324 | 3/1990 | Clark et al. | 250/288 |
| 5,006,706 | 4/1991 | Marcus | 250/288 |

FOREIGN PATENT DOCUMENTS 2616545 12/1988 France.

OTHER PUBLICATIONS

Donohue et al., "Radiofrequency Cavity Ion Source in Solids Mass Spectrometry", Analytical Chemistry, vol. 47, No. 9, Aug. 1975, pp. 1528-1531.

Primary Examiner—Jack I. Berman
Assistant Examiner—Kiet T. Nguyen
Attorney, Agent, or Firm—Dority & Manning

[57] ABSTRACT

A method and apparatus for analyzing solid sample materials mounted externally to the apparatus is provided wherein a low pressure glow discharge is initiated by applying a radio frequency potential to an integral, continuous solid sample and an electrically grounded anode in the presence of an inert gas, the glow discharge being maintained such that the inert gas is ionized and the ionized gas sputters sample material, the sputtered sample material then passing into an analyzer region for analysis.

35 Claims, 18 Drawing Sheets

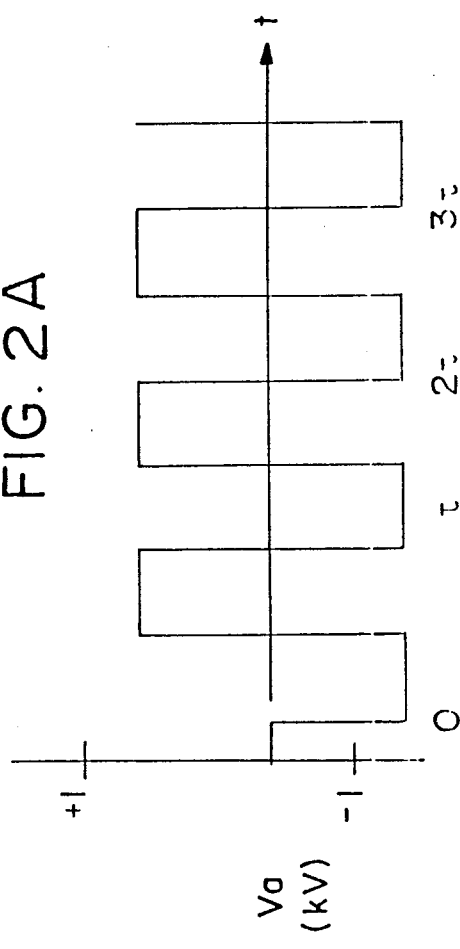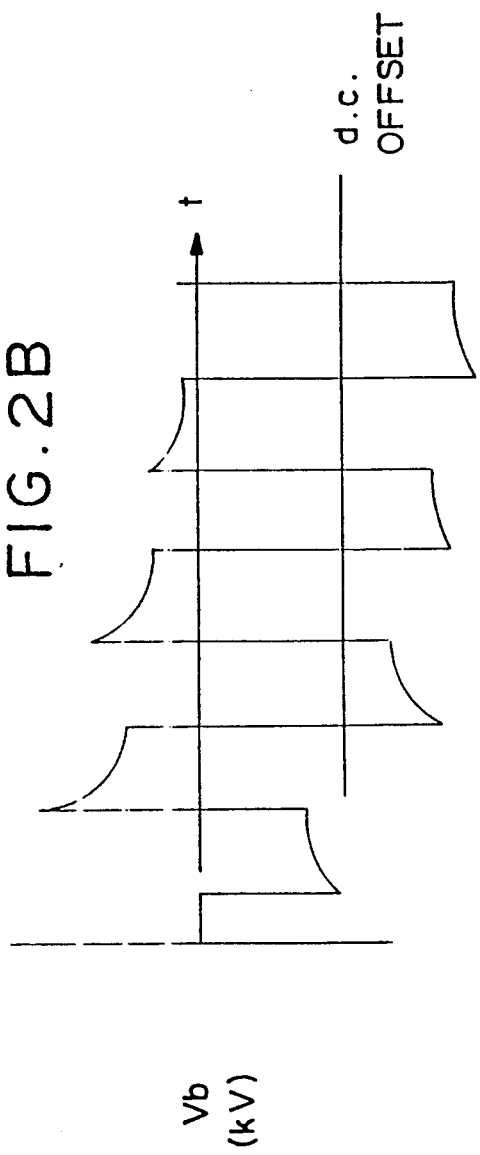

25 WATTS, 0.1 torr

25 WATTS, 0.2 torr

25 WATTS, 0.35 torr

DEVICE FOR RADIO FREQUENCY POWERED GLOW DISCHARGE SPECTROMETRY WITH EXTERNAL SAMPLE MOUNT GEOMETRY

BACKGROUND OF THE INVENTION

This invention was made with Government support under Grant No. CHE-8901788 awarded by the National Science Foundation, and thus the Government may have certain rights in the invention.

The present application is a continuation-in-part application of application Ser. No. 07/359,157, filed on May 31, 1989, now U.S. Pat. No. 5,006,706.

The present invention is directed generally to the direct analysis of solids and particularly to a radio frequency (RF) powered glow discharge sputtering source for analysis of non-conducting solids as well as metals, alloys, semiconductors and the like.

The application of conventional d.c. powered glow discharge devices for the direct analysis of conductive solids such as metals, alloys and semiconductors is well known in the art. Generally, these glow discharge devices employ low pressure, inert atmosphere plasmas to initiate cathodic sputtering of solid samples that atomizes the sample material and produces a so-called "negative glow." In the negative glow, sputtered material collides with electrons and metastable discharge gas atoms to produce excited state and ionic species. The electromagnetic radiation produced during the decays from excited energy states to lower energy states is responsible for the "glow" phenomenon.

Most commonly, the conducting sample being analyzed takes the form of a cathode. In a diode design, the sample cathode and an anode sleeve are housed in a vacuum chamber which usually also acts as an anode and is filled with an inert gas such as argon such that a sufficiently high potential placed across the electrodes causes the gas to disassociate into electrons and positively charged ions, which form part of what is sometimes called the "glow discharge." The region of the vacuum chamber in which much of this dissociation occurs is sometimes called the "discharge excitation region" or the "negative glow region." The negative field potential attracts the positively charged ions which hit the cathode surface and dislodge atoms, ions and molecules of the cathode material. This is the so-called "sputtering" phenomenon.

By virtue of the electrical biasing, negatively charged species will be accelerated away from and positively charged species returned to the cathode surface. The vast majority of sputtered particles are not charged and can either diffuse back to the cathode surface or into the negative glow. The percentage of atoms entering the discharge excitation region is a function of the discharge pressure and cathode geometry.

The sputtering process acts as a cascade of inelastic collisions with the incoming ion imparting some portion of its kinetic energy, which approaches that of the applied potential, into the cathode material's lattice structure. Provided the sputtering ion has sufficient energy and directionality, the cascade will propagate back to the surface and result in the ejection of cathode material. The ejected atoms of the cathode material diffuse into the glow discharge region and become part of the so-called glow discharge. Sputter yields, the ratio of the average number of sputtered atoms to incident ions, are a function of the relative masses of the collision partners, the incident angle and energy of the sputtering ion, and the cathode material's binding energy.

Glow discharges are currently employed for elemental analysis by atomic absorption, atomic emission, atomic mass spectrometry, and a number of laser-based spectroscopic methods. These glow discharge sources have been limited by the requirement that the sample be conductive in nature so that it may act as a cathode in a conventional d.c. diode design. Thus, for some nonconducting materials it became necessary to place the nonconducting analyte in a solution. However, some nonconducting materials are not conveniently dissolved. In an effort to analyze nonconducting solids without dissolution, nonconducting powder samples have been mixed with a conducting powder matrix. The resulting powder mixture is pressed into a disc sample, which, because of the conductive portion, allows for the required flow of current, but which also permits the sputtering of atoms of the nonconductive material upon impingement by a discharged ion. However, the mixing of the original sample with the conducting material, whether in solution or powder form, introduces certain problems. For example, the dilutive effect of the conducting material results in both a loss of sensitivity and an increase in the likelihood of contamination. Moreover, many nonconducting solids are not easily transformed into powders, and the transformation of the solid into a powder precludes any depth resolved analyses.

The use of a radio frequency discharge in argon to sputter and ionize a solid hollow cathode sample for analysis has been described (*Analytical Chemistry*, 47 (9), 1528, 1975). However, the hollow cathode geometry requires that the sample itself be machined into a cylinder. Machining the sample into a cylinder requires considerable labor and prevents depth profiling analysis.

The use of any glow discharge sampling geometry in which the sample must be inserted into the vacuum chamber, automatically restricts the size and shape of the sample to be analyzed. In such instances, metals and alloys must be machined to the proper geometry. Machining and grinding eliminate the possibility of performing depth-resolved analyses. Electrically nonconductive materials such as glasses and ceramics are often nonmachineable. Nonmachineable bulk solids must first be ground into a powder and then pressed to form a solid powder sample of compatible size and shape. Additionally, the combination of powdered nonconductive samples with a conducting material results in both a loss of sensitivity and an increase in the likelihood of contamination.

A Grimm-Type high frequency powered glow discharge device such as disclosed in French Publication No. 2 616 545 (Dec. 16, 1988), which mounts the sample outside the vacuum chamber, disposes the cathode between the sample and the anode, and thus runs the risk of contamination from sputtering of the cathode material.

OBJECTS AND SUMMARY OF THE INVENTION

It is, thus, an object of the present invention to provide a novel method for direct analysis of solids.

It is a further object of the present invention to provide a novel apparatus employing glow discharges to atomize solid samples for direct analysis.

It is yet another object of the present invention to provide an apparatus which employs radio frequency potentials for initiating and maintaining glow discharges.

It is still another object of the present invention to provide a radio frequency powered apparatus for the direct analysis of flat cathode samples and pins.

It is another object of the present invention to provide a method and apparatus for the direct analysis of insulating materials without matrix modification.

It is still a further object of the present invention to provide a method for atomizing solid samples for analysis by spectroscopic techniques including atomic fluorescence, atomic emission, atomic absorption and mass spectrometry.

It is yet another object of the present invention to provide an apparatus for sputtering solid samples for elemental analysis by conventional spectroscopic methods including mass spectrometry, atomic absorption, atomic emission and atomic fluorescence.

It is still another object of the present invention to provide such an apparatus which provides for the fast, successive analysis of a plurality of samples.

Yet another object of the present invention is to provide an apparatus and method for atomizing solid samples for analysis regardless of the electrical conductivity of the sample and without the need for such modifications of the sample as machining, dissolving, pulverizing, pressing or molding.

A further object of the present invention is to provide an apparatus and method for atomizing solid samples for analysis without having to insert the sample into the chamber where the glow discharge plasma is formed.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus and method for analyzing sample materials in the solid state includes an enclosure that defines a vacuum chamber with a vacuum port connectable to means for evacuating the vacuum chamber. The enclosure defines at least one gas inlet port connectable to means for supplying gas into the vacuum chamber. The gas to be supplied to the vacuum chamber is an inert gas such as argon. The enclosure includes an electrode which is provided with a surface that is exposed to the interior of the vacuum chamber. The enclosure defines an output port that is connectable to means for analyzing the contents of the vacuum chamber.

In further accordance with the present invention, the vacuum chamber enclosure defines an external mount for receiving a solid sample external to the vacuum chamber. The enclosure defines a sample port that communicates between the interior of the vacuum chamber and the exterior of the vacuum chamber. The external mount includes a mounting surface that defines a portion of the exterior surface of the enclosure. The mounting surface is disposed to adjoin a portion of the enclosure which defines the sample port. The external mount further includes an external mounting plate that defines a sample hole therethrough and communicates with the sample port defined by the enclosure. In some embodiments, the mounting plate can be formed as a unitary structure with the enclosure. In other embodiments, a sample mold is provided to hold compacted powderous sample material. In yet other embodiments, the mold is provided with features which permit cooling of the sample material.

In yet further accordance with the present invention, means are provided for securing the sample to the external mount wherein at least a portion of the sample forms a vacuum seal around the sample hole. As embodied herein, the securing means can include a flexible sealing gasket, a torque bolt, and an insulating spacer. The torque bolt is disposed outside the vacuum chamber so as to be able to bias and secure the sample against the sample sealing gasket. The gasket is configured so as to be disposable against and between the surface of the sample that is to be received by the external mount and exposed to the interior of the vacuum chamber and the surface of the sample mounting plate that faces away from the interior of the vacuum chamber. The insulating spacer is disposed between the sample and the end of the torque bolt and electrically insulates the sample from the bolt as well as protecting the sample from being crushed or damaged by the direct contact of the bolt. Moreover, the sample sealing gasket is configured so that it maintains both a vacuum tight seal and a separation distance of less than one dark space between the surface of the sample and the surface of the mounting plate.

In yet further accordance with the present invention, means are provided for applying a radio frequency electromagnetic potential between the electrode defined by the vacuum chamber and the sample to be received by the external mount. As embodied herein, the RF application means can include a radio frequency generator, a matching network, a radio frequency coaxial cable, a male coaxial connector, a female coaxial connector, an elongated conductor (which can be surrounded by an electrically insulating sheath), and a ground lead connected to the electrode defined by the enclosure. Moreover, the electrode defined by the enclosure is electrically connected to the mounting plate. An elongated cavity is defined longitudinally through the torque bolt and the spacer and is configured to receive the conductor and the insulating sheath. One of the coaxial connectors is connected between one end of the coaxial cable and the conductor, while the other of the coaxial connectors is connected to the opposite end of the torque bolt than the end that is disposed to press against the insulating spacer. When the connectors are connected to one another, the free end of the conductor engages the surface of the sample opposite the surface which is exposed to the interior of the vacuum chamber. The radio frequency generator is connected to the opposite end of the coaxial cable via the matching network, which is connected to the radio frequency generator in series.

The surface of the electrode defined by the enclosure and exposed to the interior of the vacuum chamber where the glow discharge occurs, must be much larger than the surface of the sample that is exposed to the interior of the vacuum chamber via the sample hole. A ratio of 50 to 1 for the area of the grounded enclosure electrode to the area of the sample circumscribed by the sample hole may be large enough. However, a 500 to 1 ratio is satisfactory.

In operation, the inert gas is introduced into the chamber and maintained at a low pressure. The walls of the chamber are connected to ground, and the sample is secured to the external mount so that the sample surface exposed to the interior of the chamber is located less than one dark space from the surface of the mounting plate of the external mount, which is the portion of the enclosure electrode located closest to the sample. The conductor is positioned so as to touch the rear of the sample, i.e., the surface of the sample opposite the surface disposed so that it becomes located less than one dark space separation distance from the surface of the mounting plate of the external mount. The RF generator is activated to provide anywhere from 1 to 100 watts of power. The glow discharge is maintained in the chamber such that the inert gas becomes ionized, and the ionized gas sputters the sample surface exposed to the interior of the vacuum chamber. The sputtered sample material becomes available for analysis. The sputtered particles can be collected and analyzed (with a mass spectrometer for example). The electromagnetic radiation emanating from the glow discharge can be collected and analyzed (for atomic emission or atomic absorption for example).

More than one output port can be provided for the enclosure. One or more of the output ports can include a fused silica window. Depending upon the type of analysis to be performed on the sample, the window can be oriented directly in a line of sight to the surface of the sample exposed to the interior of the vacuum chamber or at a right angle to this head-on line of sight. The signal-to-noise ratio can be maximized by directing the input of the analyzing instrument at a position within this range of positions for the window. The RF power supplied to the sample can be modulated on and off, and the analyzing instrumentation can be synchronized to operate according to the modulation of the RF power supply. The pressure of the inert gas in the vacuum chamber can be maintained by adjusting the evacuating means and the flow of gas into the chamber via the gas inlet. Desirably, the pressure within the chamber should be maintained at a sufficiently low pressure so as to reduce the redeposition of the sputtered sample material onto the surface of the sample.

The present invention permits the analysis of nonconducting materials without matrix modification. The present invention solves the problem of placing a nonconducting analyte in solution by omitting this step and analyzing the solid material directly. Additionally, by allowing for the direct analysis of samples of the nonconducting material, the present invention solves the problem of machining the nonconducting solid into a cylinder for a hollow cathode electrode configuration. This capability, especially in combination with the external mount geometry described herein, provides a much simpler, cheaper and easier to operate system than any prior known means for analysis of electrically insulating materials.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 2(a-b) are graphical representation of the effect of the application of a 2 kV peak-to-peak square wave potential to a pair of electrodes;

DETAILED DESCRIPTION OF THE PREFERRED EMBODIMENTS

Reference now will be made in detail to the present preferred embodiments of the present invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover the modifications and variations of this invention provided they come within the scope of the appended claims and their equivalents.

Figure 1:
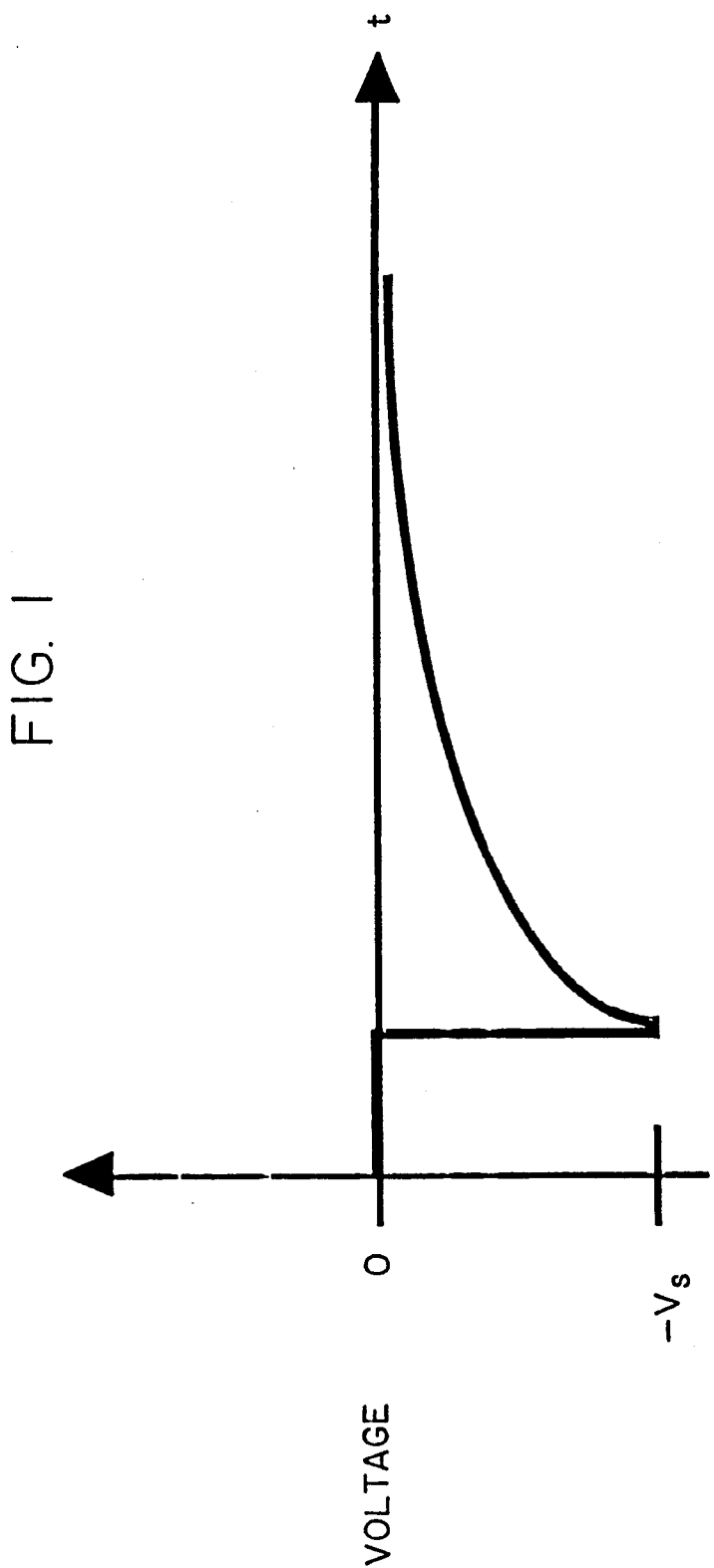
FIG. 1 is a graphical representation of the effect of the application of a high voltage pulse to an insulating surface.

As noted above, one of the factors which has tended to limit the application of glow discharges has been the requirement that the sample be conductive in nature. Conventional d.c. glow discharges cannot be used for the sputtering of purely nonconductive material, because in a d.c. system, if one of the electrodes in the system is an electrically insulating material, the required flow of current cannot occur. However, as shown in FIG. 1, the application of a high voltage pulse to an insulating surface can be considered analogous to the charging of a capacitor. As a high negative voltage $(-V_s)$ is applied, the electrode surface potential drops to $-V_s$ followed by a charging to more positive potentials as a function of time. This is not due to the accumulation of positive charges at the surface but rather the loss of electrons through ion neutralization reactions at the surface. The time scale of this process is such that the application of voltage pulses at frequencies on the order of one megahertz (MHz) and above results in a pseudo-continuous plasma.

A key aspect of the application of RF glow discharges to the sputtering of surfaces is the self-biasing which occurs between the plasma electrodes. For example, the application of a 2 kilovolt (kV) peak-to-peak square wave potential $(V_a)$ to a pair of electrodes is illustrated in FIG. 2. In the initial half-cycle, the voltage of the primary cathode $(V_b)$ goes to $-1$ kV and then begins positive charging to approximately $-0.7$ kV. As the applied voltage is switched to $+1$ kV, a surface potential of $+1.3$ kV is produced. During this half-cycle, electrons are accelerated to the electrode's surface. The greater mobility of the plasma electrons (compared to the much heavier positive ions) results in a faster surface charging during this half-cycle such that the electrode's surface potential approaches zero much faster than the previous half-cycle and thus reaching a value of $+0.2$ kV. When the voltage polarity is switched to the start of the second full cycle, the potential on this electrode will reach $-1.8$ kV $(+0.2-2$ kV). As successive cycles proceed, the wave form of $V_b$ will reach a constant offset value which is significantly displaced in the negative direction. This negative d.c. offset is known as "self-biasing", generally has a value of one-half of the applied peak-to-peak potential, and is for all intents and purposes continuous. The electrode is bombarded alternately by high energy ions and low energy electrons and is, therefore, employed as the sputtering target (cathode). While the potentials supplied to the electrodes are alternating, a time averaged cathode and anode are established. As will be discussed in greater detail below, self-biasing is also a function of the respective electrode sizes. Thus, it is preferable to apply the RF potential to the sputtering target and to make its exposed area much smaller than the vacuum chamber anode, which is usually held at ground potential.

Figure 3:
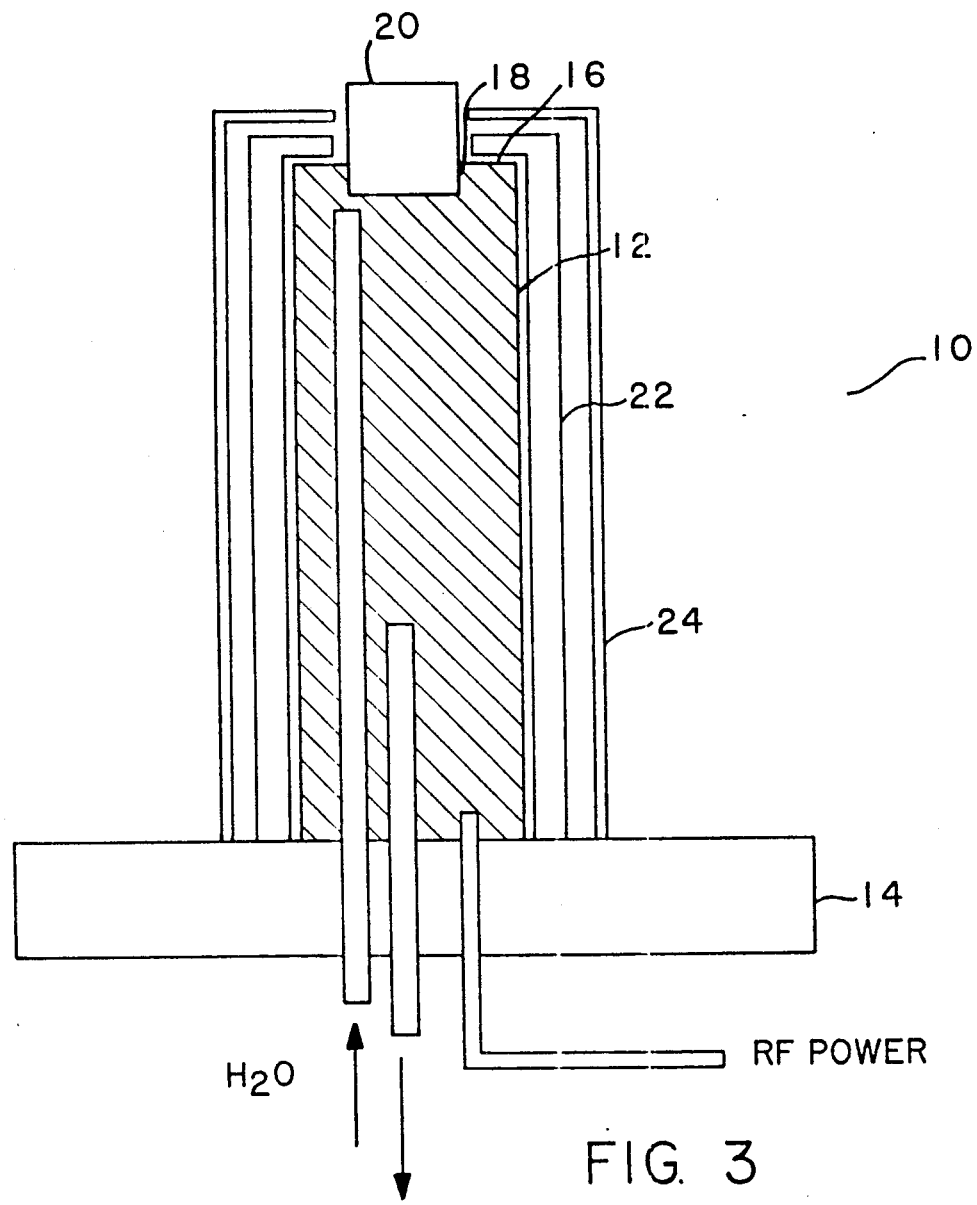
FIG. 3 is a schematic diagram of a sample holder in accordance with the present invention.

Turning now to the design of an embodiment of the apparatus of the present invention, FIG. 3 diagrammatically illustrates a preferred sample holder which is generally designated by the numeral 10. The body 12 of the holder 10 is a stainless steel cylinder capped at one end by a plate 14 which has electrical and cooling water connections, shown schematically. The opposite end of the body is enclosed by a cathode mounting plate 16 which has a recession 18 preferably 0.5 inches in diameter and 0.125 inches deep into which the sample 20 is press fit. Preferably the holder body is encased in a glass ceramic sleeve 22 which acts to reduce the amount of sputtering of the holder body. An electrically grounded stainless steel "anode" sleeve 24 is mounted thereabout.

The minimum distance required for the formation of a plasma is referred to as a dark space. Thus, the stainless steel sleeve 24 is preferably less than one dark space from the holder body 12 to prohibit the formation of a plasma in the enclosed regions. The entire sample holder/sleeve assembly is mounted on a flange which mates with a six-way cross ion source region described below. Preferably, the inner walls of the vacuum chamber act as an anode.

Figure 4:
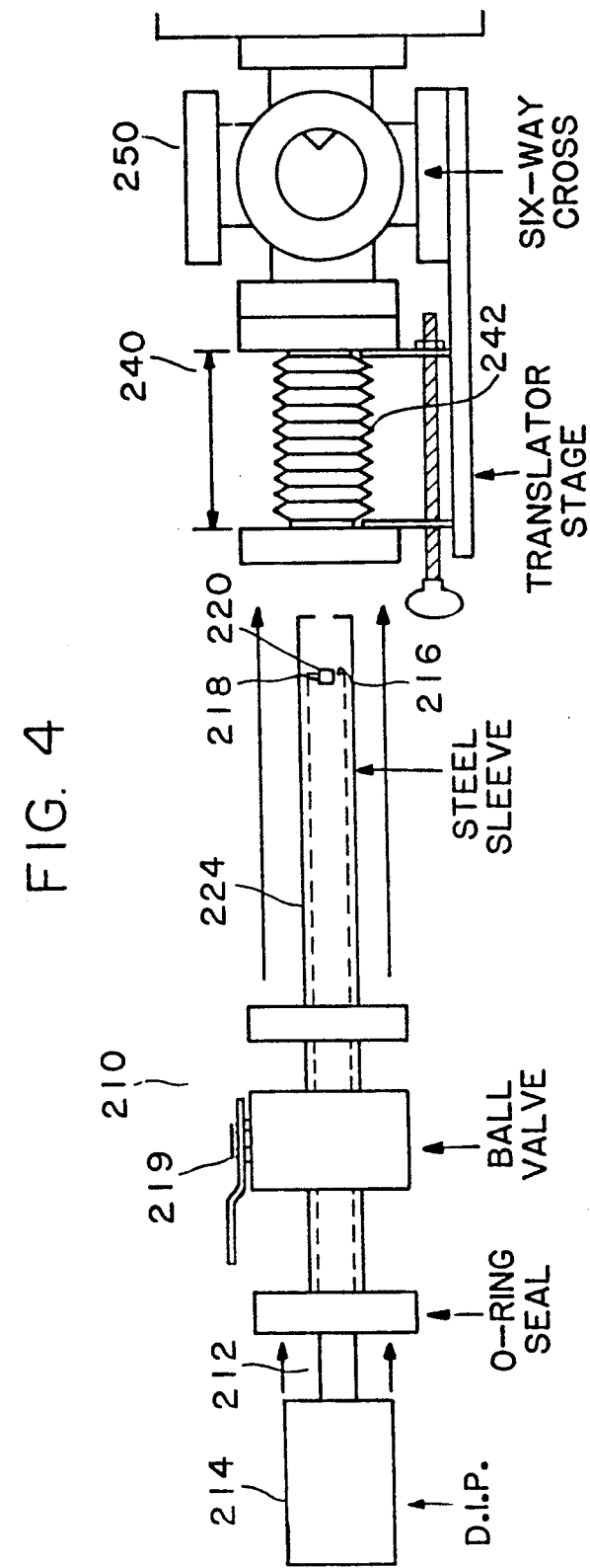
FIG. 4 is an exploded schematic diagram of a direct insertion probe in accordance with the present invention in axial alignment with a translator and a six-way cross.

Alternatively, FIG. 4 schematically illustrates an embodiment of a direct insertion probe (DIP) for use with the present invention. The probe 210 mates with a six-way cross 250 through a translator stage 240. The translator stage including bellows 242 in conjunction with ball valve 219 serves as a vacuum interlock allowing for insertion and withdrawal of the probe without adjustment of the argon pressure within the six-way cross vacuum chamber, thereby permitting faster analysis of a series of samples. A sample holder body 212 is mounted onto the probe 214. A small sample pin 220 is mounted to the sample holder at its tip 216 within a recess 218. A grounded anode cap 224 is drawn over the sample holder and secured thereon. As in the above discussed configurations, the anode cap is within one dark space from the cathode to preclude discharge therein. Thus, a series of sample holders may be provided such that numerous samples can be prepared for a fast, easy analysis of a batch of materials.

In the studies described here, unless otherwise noted, the glow discharge plasma was powered by a Model RF-10 radio frequency generator, available from RF Plasma Product. This unit has a maximum power output of 1 kilowatt (kW) at a frequency of 13.56 MHz. In order to achieve efficient energy transfer to the plasma, an impedance matching network is incorporated in series with the generator. The matching network is an LC circuit which is tuned such that the total impedance of the network and the plasma equal the output impedance of the generator.

Figure 5:
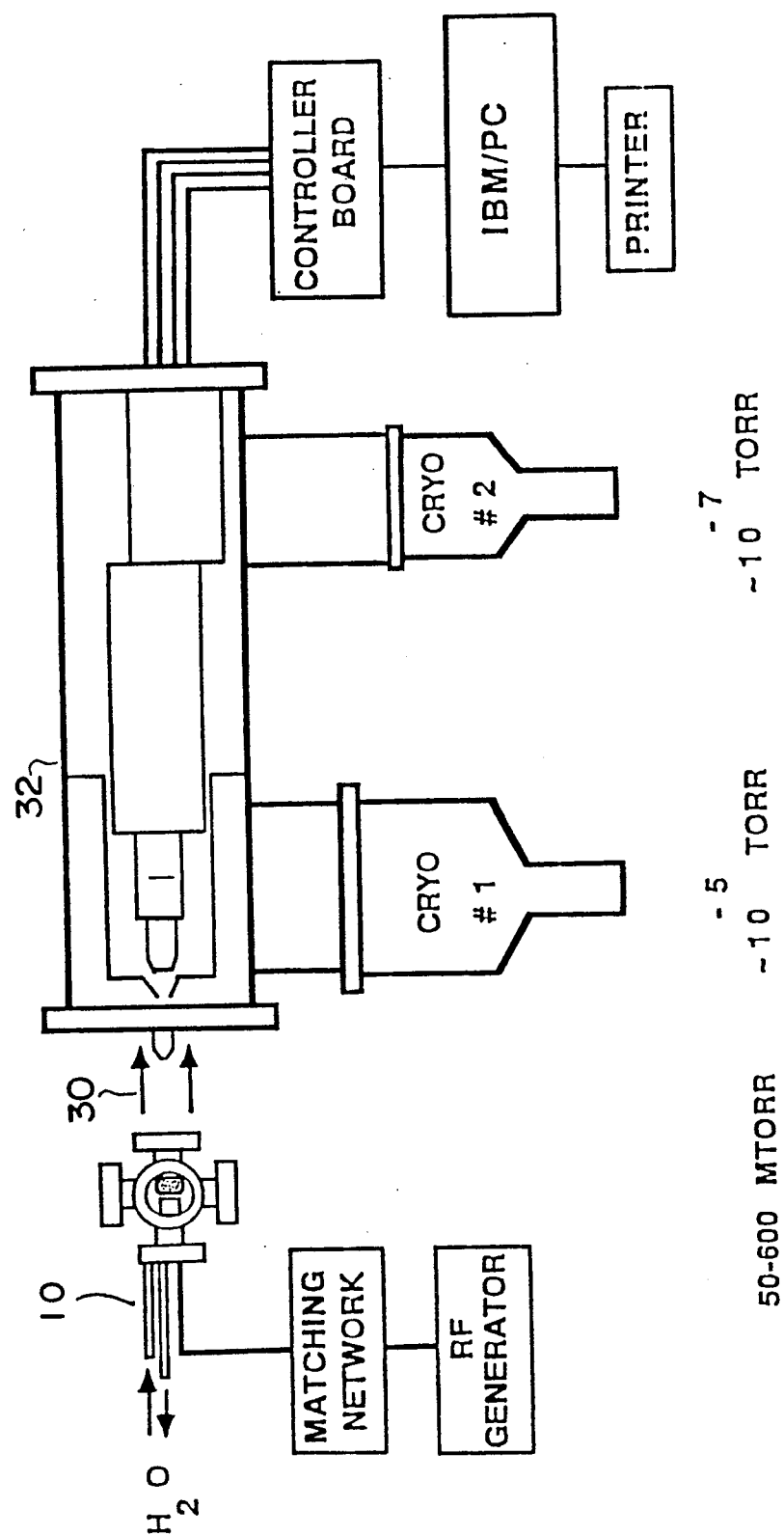
FIG. 5 is a diagram of the present invention as assembled for mass spectrometry analysis.

FIG. 5 is a diagrammatic representation of an embodiment of the apparatus of the present invention as assembled for mass spectrometry analysis. The glow discharge ion source 10 is mounted coaxial with the mass spectrometer axis. The remaining ports of the six-way cross are utilized for the mounting of fused silica optical windows, vacuum and gas inlet attachments, and pressure monitoring thermocouples. Ions generated in the source region pass through an intermediate vacuum region 30 and into the analyzer region 32 for analysis.

Figure 6:
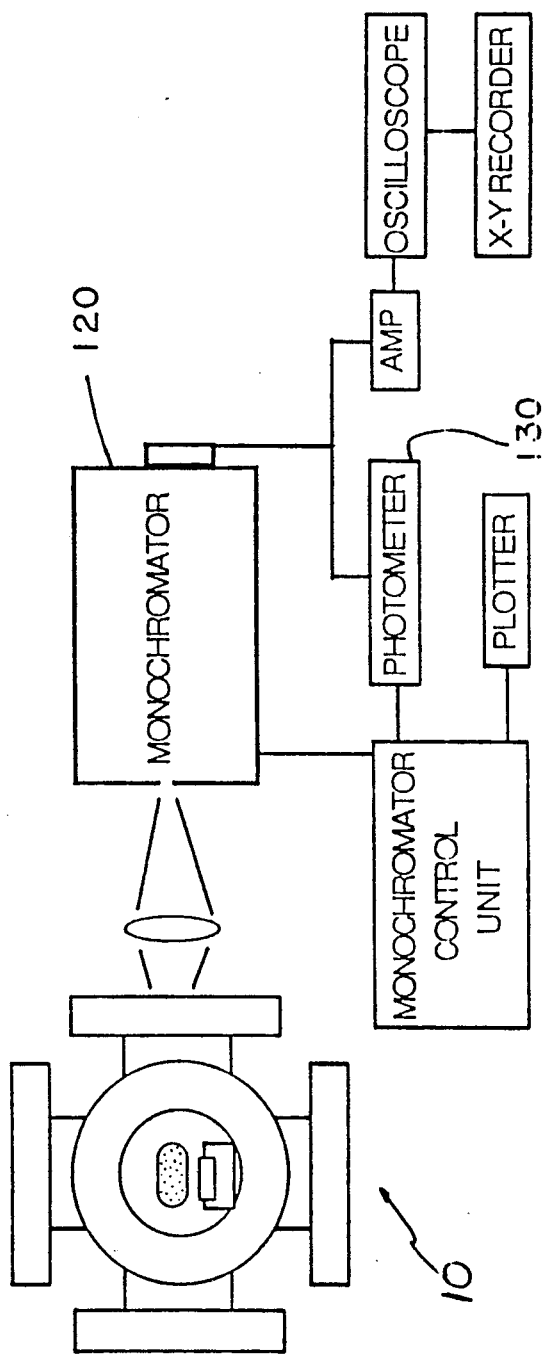
FIG. 6 is a diagram of the present invention as assembled for atomic emission analysis.

Alternatively, FIG. 6 diagrammatically represents an embodiment of the apparatus of the present invention as assembled for atomic emission analysis. The glow discharge ion source 10 is mounted at a 90° angle to the atomic emission axis. Monochromator 120 isolates a narrow region of wavelengths for detection by photometer 130.

Figure 7:
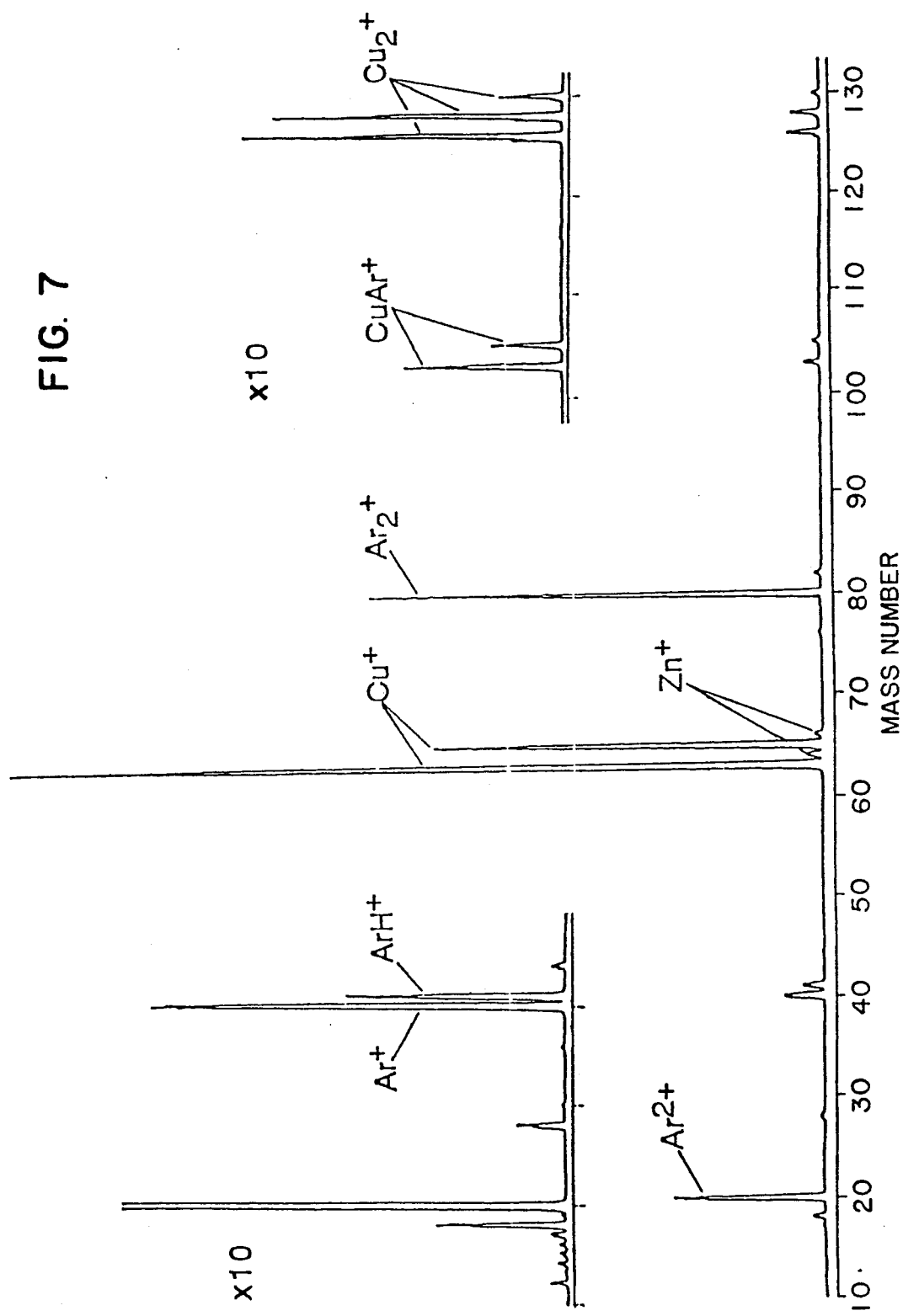
FIG. 7 is a radio frequency glow discharge mass spectrometry spectrum of a copper sample generated in accordance with the present invention.

A preliminary evaluation of the operating parameters of the glow discharge ion source of the present invention was performed employing a conductive sample. A copper metal matrix was chosen because of its ease of sputtering and an earlier d.c. glow discharge mass spectrometric analysis performed on this material. FIG. 7 is the radio frequency-glow discharge mass spectrometry (rf-GDMS) spectrum of the copper sample under discharge conditions of 0.2 torr argon pressure and 10 watts power. The spectra are atomic in nature with the spectrum dominated by ions of the matrix species and various discharge gas species. Scale expansion of the spectrum reveals the existence of species related to residual gases due to non-ideal vacuum conditions: $H_2O^+$ at mass 18, $N_2^+$ at 28, and $CO_2^+$ at mass 44.

Figure 8:
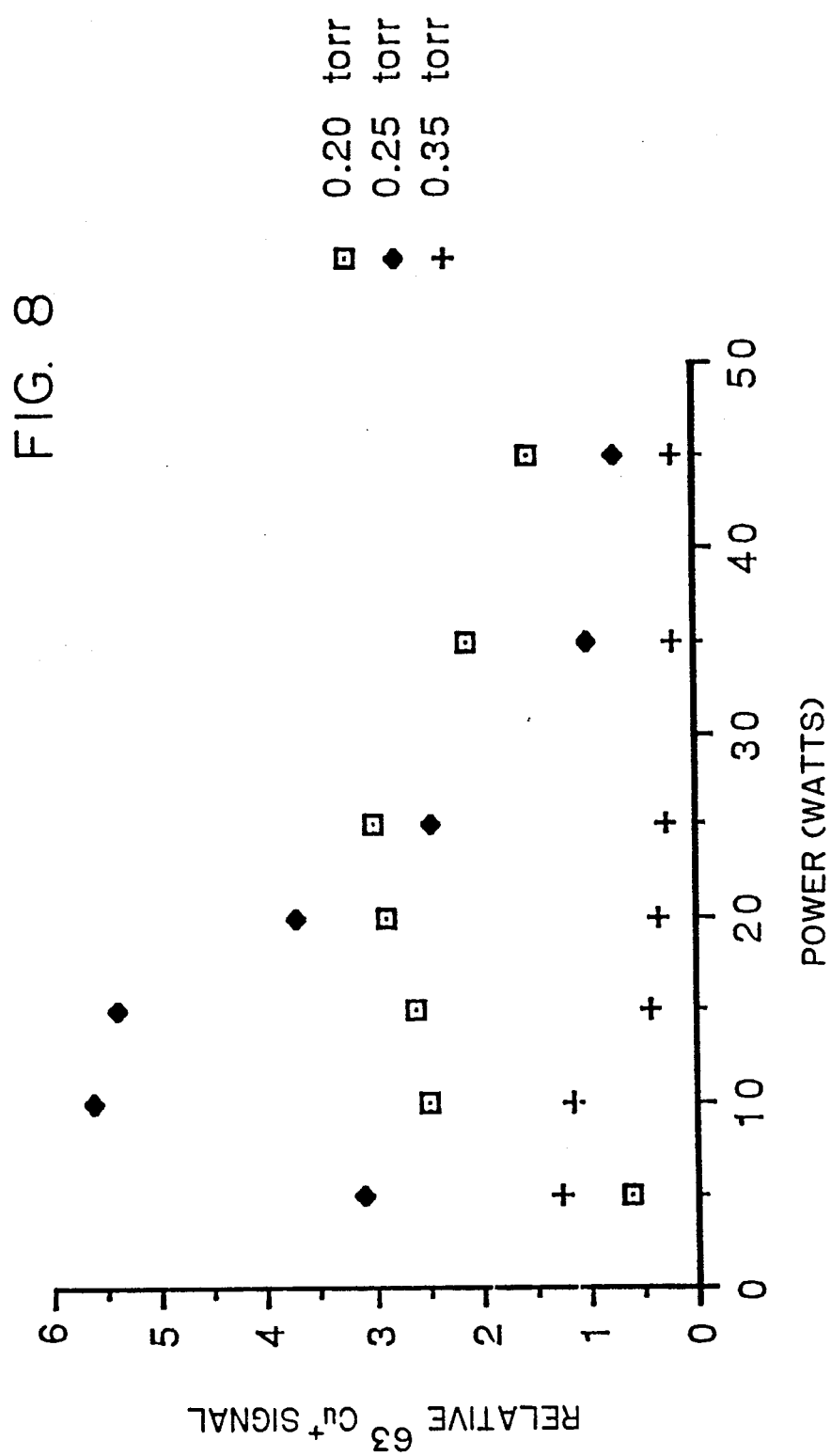
FIG. 8 is a graphical representation of the effect of changes in power and pressure on a copper matrix ion signal generated by the method of the present invention.

The complex interdependency of the pressure-current-voltage conditions of the d.c. plasma sources makes parametric evaluations quite complex. However, the RF source is powered by a constant power generator which makes evaluation somewhat more straightforward. The response of the copper matrix ion signal, specifically, $^{63}Cu^+$, to changes of discharge power is shown for a range of pressures in FIG. 8. For each fixed pressure data set, a power is observed where a maximum amount of matrix ion signal is detected. It can be seen that as the discharge pressure increases, the point of the maximum signal shifts to lower power settings. This trend in responses is related to the physical relationship between the plasma negative glow/dark space interface and the ion sampling orifice.

Figure 10C:
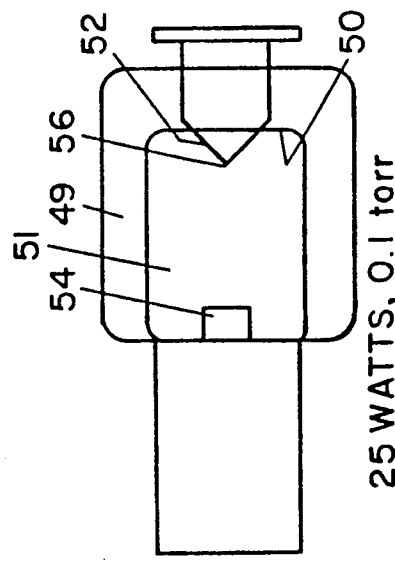
FIGS. 10a, 10b and 10c are diagrams illustrating the effect of discharge pressure on dark space thickness.
Figure 10B:
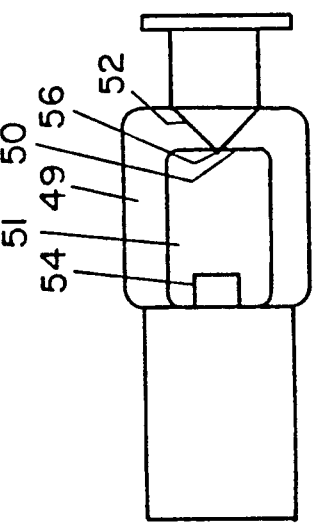
Figure 10A:
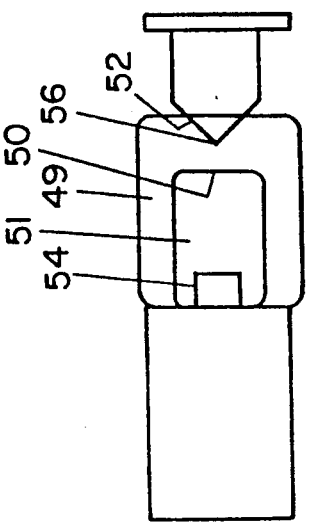

FIGS. 10a, 10b and 10c schematically illustrate the effect of discharge pressure on the dark space 49 thickness and the relationship between the interfacial region 50 and the sampling cone 52. As discharge pressures decrease, electron mean free paths increase such that the cathode fall (potential drop) occurs over longer distances away from the cathode surface 54, and thereby extending the interfacial region 50 toward the exit orifice 56. Decreases in discharge power (voltage) produce analogous changes, though to a much lower degree. Visual observation of the plasma shows a correlation between the position of the interface 50 between the negative glow 51 and the dark space 49 and the matrix ion signal detected. The discharge conditions in which maximum signal is observed are those shown in FIG. 10b where the sampling cone orifice 56 is at the interfacial region 50, the area of greatest ion density. This spatial relationship is caused by the loss of sufficient energy by secondary electrons emitted from the cathode surface 54 to be effective in direct electron impact ionization collisions with sputtered atoms.

Figure 9:
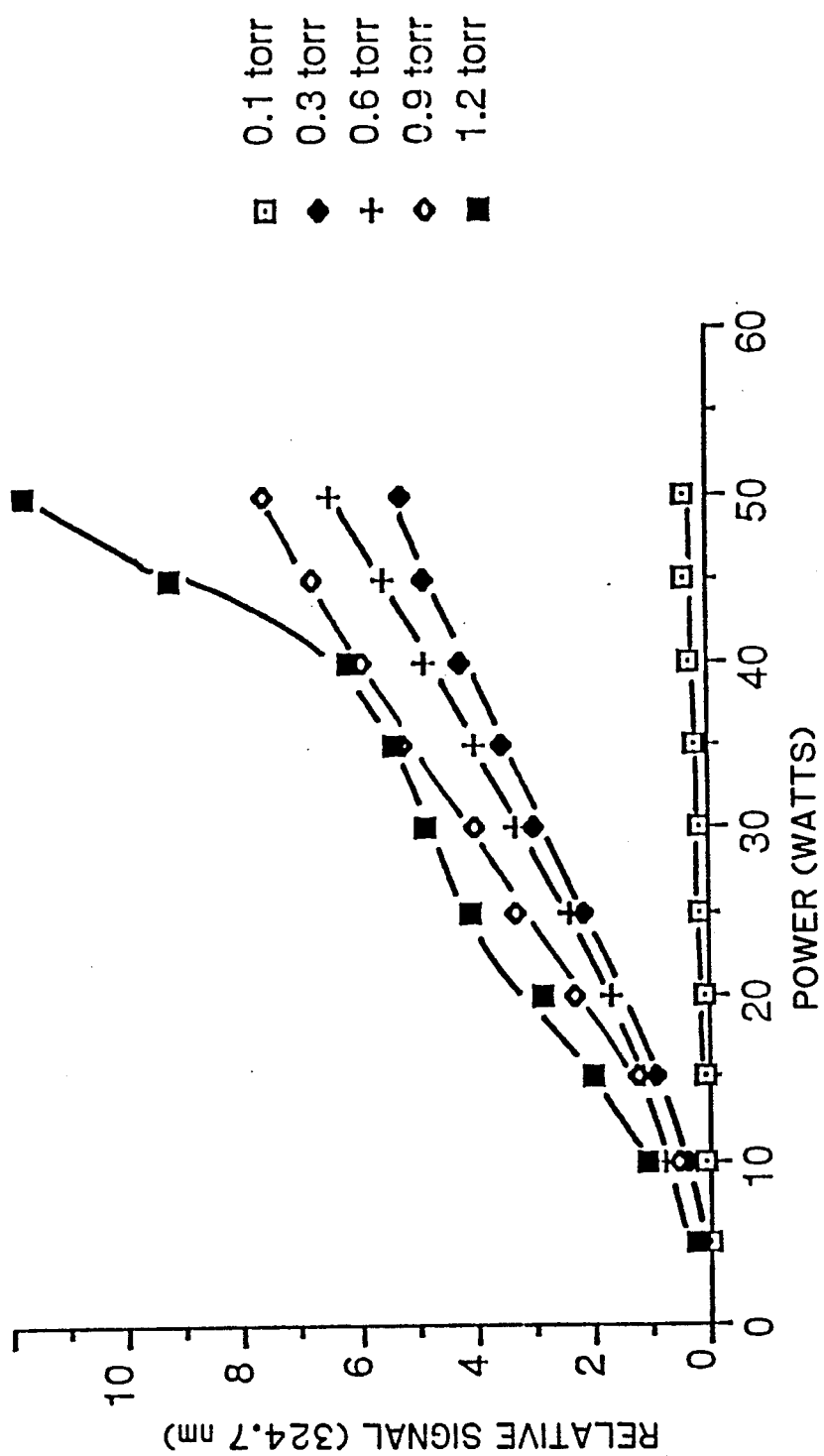
FIG. 9 is a graphical representation of the effect of changes in power and pressure on the copper (I) emission signal generated by the method of the present invention.

Thus, sampling for mass spectrometric analysis is highly region-specific requiring adjustments of both pressure and power in order to position the negative glow/dark space interface at the sampling cone. In contrast, in an atomic emission analysis, the entire plasma is analyzed, resulting in a more straightforward relationship between power and pressure and the relative signal for each species, as is illustrated with respect to copper (I) in FIG. 9. Generally, the signal becomes stronger with increased power and increased pressure.

Although for most optical techniques, signal strength generally increases with increased pressure, it is often beneficial to maintain relatively low pressures to decrease redeposition. As pressure increases, activity in the plasma increases, causing sputtered species to redeposit on the cathode surface. In many applications it is desirable to reduce redeposition as much as possible. For example, in depth profiling, the depth of a coating on a sample surface is measured by sputtering the coating, analyzing the sputtered species over time, and observing the change in the spectrum to that of the sample material as a function of time. A high level of redeposition caused by a high operating pressure results in sputtered coating species deposited on the exposed sample surface, thereby blurring the line between the coating spectra and the sample spectra. Conversely, low operating pressures and correspondingly low redeposition levels provide enhanced depth profiling resolution. Thus, the present RF source provides a fast and inexpensive means for depth profiling with greater resolution capabilities than a conventional d.c. device because of lower operating pressures.

EXAMPLE 1

Figure 11:
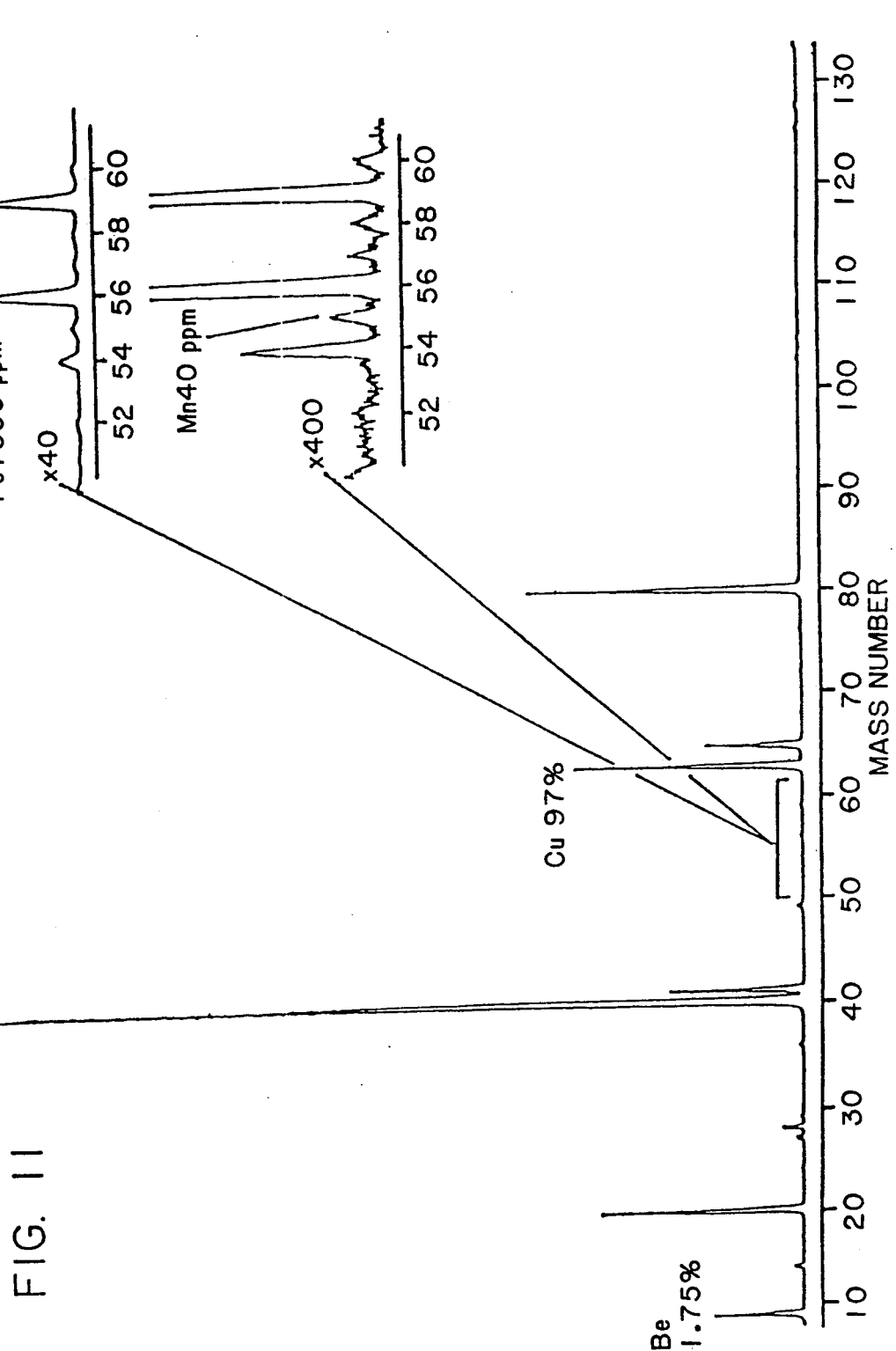
FIG. 11 is a radio frequency glow discharge mass spectrometry spectrum of a copper-beryllium alloy generated in accordance with the present invention.

The application of the glow discharge ion source of the present invention to the analysis of conducting materials is demonstrated in FIG. 11. FIG. 11 is a mass spectrum of the NBS SRM C1122 copper-beryllium alloy under discharge conditions of 0.15 torr argon pressure and 20 watts RF power using the sample holder of FIG. 3. The isotopic signals for the Cu and Be matrix species are clearly seen. The relative sensitivity factors for the iron, cobalt and manganese in the sample are similar to those observed with d.c. glow discharge sources.

Figure 12:
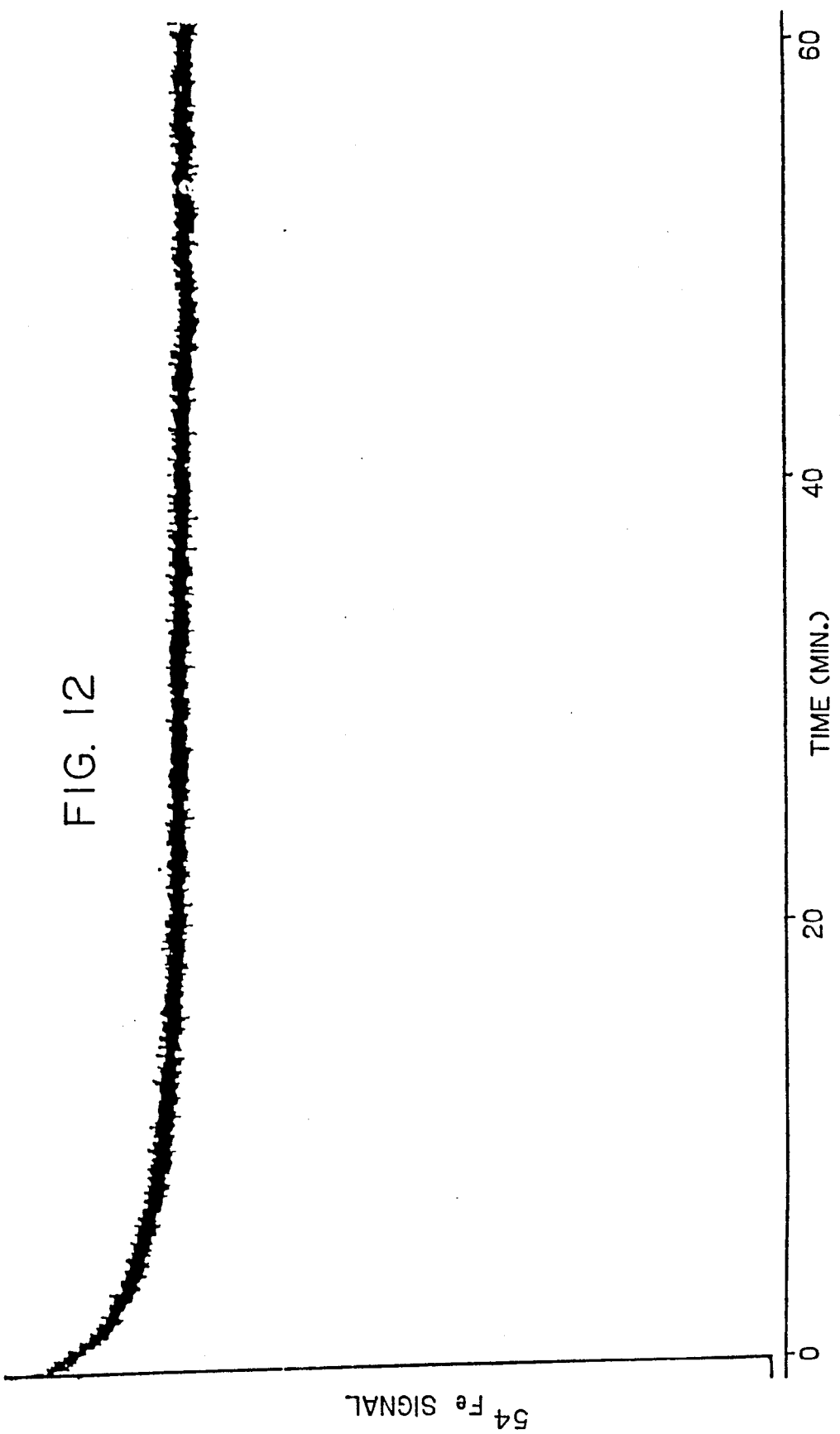
FIG. 12 is a plot of a single ion monitoring trace of a $^{54}$Fe (93 ppm) ion signal as achieved by the present invention.

The ion source operates stably over extended periods of time. FIG. 12 is a single ion monitoring trace of the $^{54}Fe$ (93 ppm) ion signal. After an initial 20 minute plasma induction period, the measured ion signal varies by only about 3 percent over the following 40 minute time period. Temporal stability is important for a method such as quadrupole mass spectrometry, which is a sequential analysis technique.

EXAMPLE 2

Figure 13:
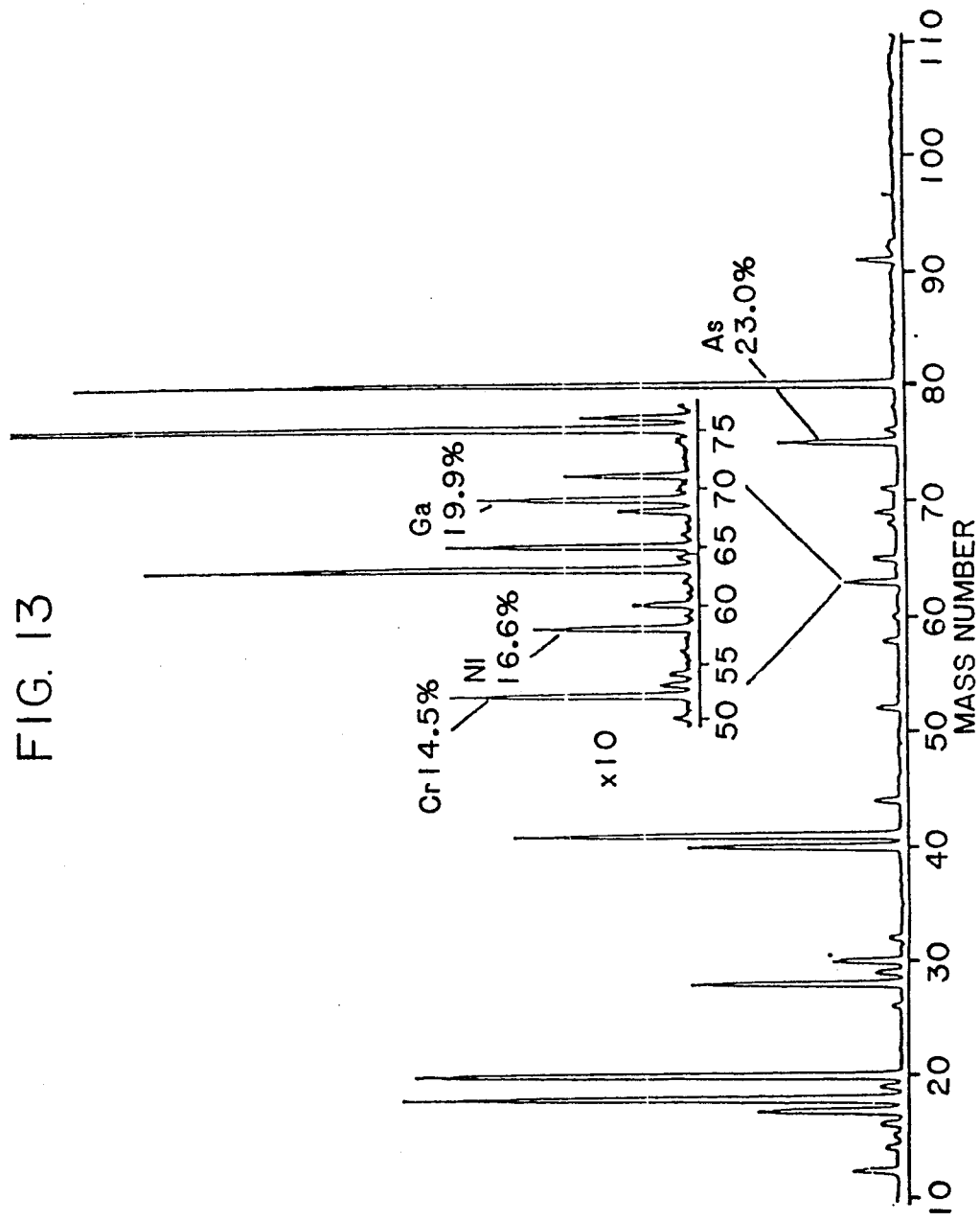
FIG. 13 is a radio frequency glow discharge mass spectrometry spectrum of a pressed disc formed from a mixture of transition metal oxides generated in accordance with the present invention.

To investigate the sputtering of nonconductors, a mixture of transition metal oxides was prepared from Spex (Edison, N.J.) Hi-Pure powders pressed into the form of a disc. Although the sample disc was mounted on a copper backing disc to achieve proper sample positioning with respect to the sampling cone, no conducting powder was added to the mixture, and the copper disc was not used to induce current flow as in the prior art d.c. method. The mass spectrum obtained from the mixture, which was run under discharge conditions of 0.3 torr argon pressure and 25 watts RF power using the sample holder of FIG. 3, is shown in FIG. 13. As can be clearly seen in the X10 scale expansion, the oxides are efficiently sputtered, dissociated and ionized in elemental form. Although the sample itself is nonconducting, the measured ion current for the metal ions are on the same order of magnitude as the metal alloy of Example 1, thus indicating that the oxygen in the sample simply represents an additional element in the matrix which will be sputter atomized like the metal atoms. The spectrum also indicates, through the presence of water and related residual gases, that care should be taken to properly dry and degas the oxide powder samples prior to analysis. The ability to produce atomic ions from a sample of this type is indicative of the applicability of the RF-GDMS source to the analysis of ceramic and cement powders.

EXAMPLE 3

Figure 14:
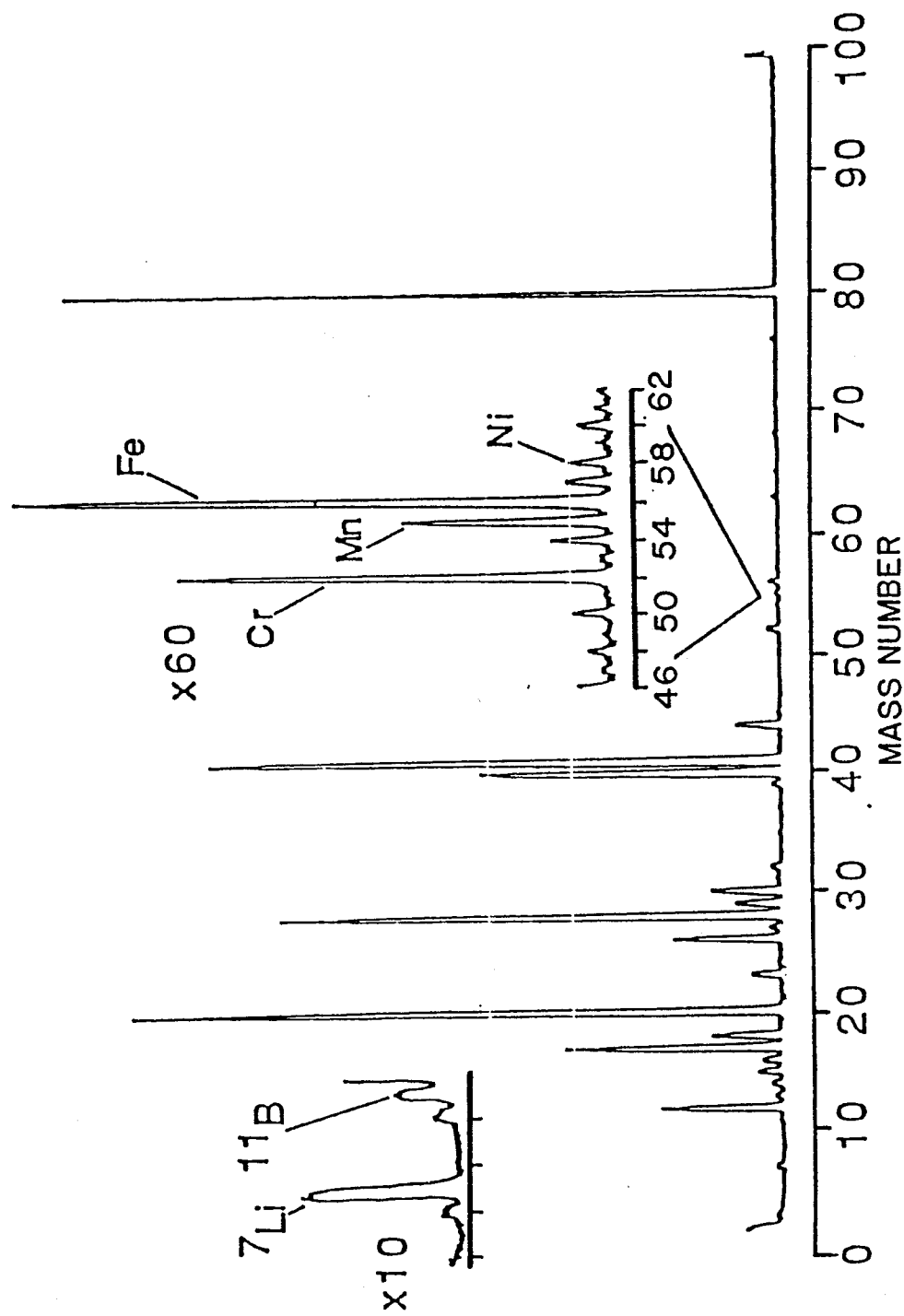
FIG. 14 is a radio frequency glow discharge mass spectrometry spectrum of a vitrified simulated defense waste glass generated in accordance with the present invention.

To investigate the ability of the glow discharge to sputter glass matrix samples, mass spectra were obtained from a glass frit precursor and a vitrified simulated defense waste glass which is commonly employed in the immobilization of high level nuclear waste. As in the case of the metal oxide powders of Example 2, the frit sample was prepared by compacting it into disc form. FIG. 14 is a GDMS spectrum of the vitrified simulated defense waste glass under discharge conditions of 0.15 torr argon pressure and 20 watts RF power using the sample holder of FIG. 3. As was the case for other nonconducting matrices, the plasma was stable.

EXAMPLE 4

Figure 15:
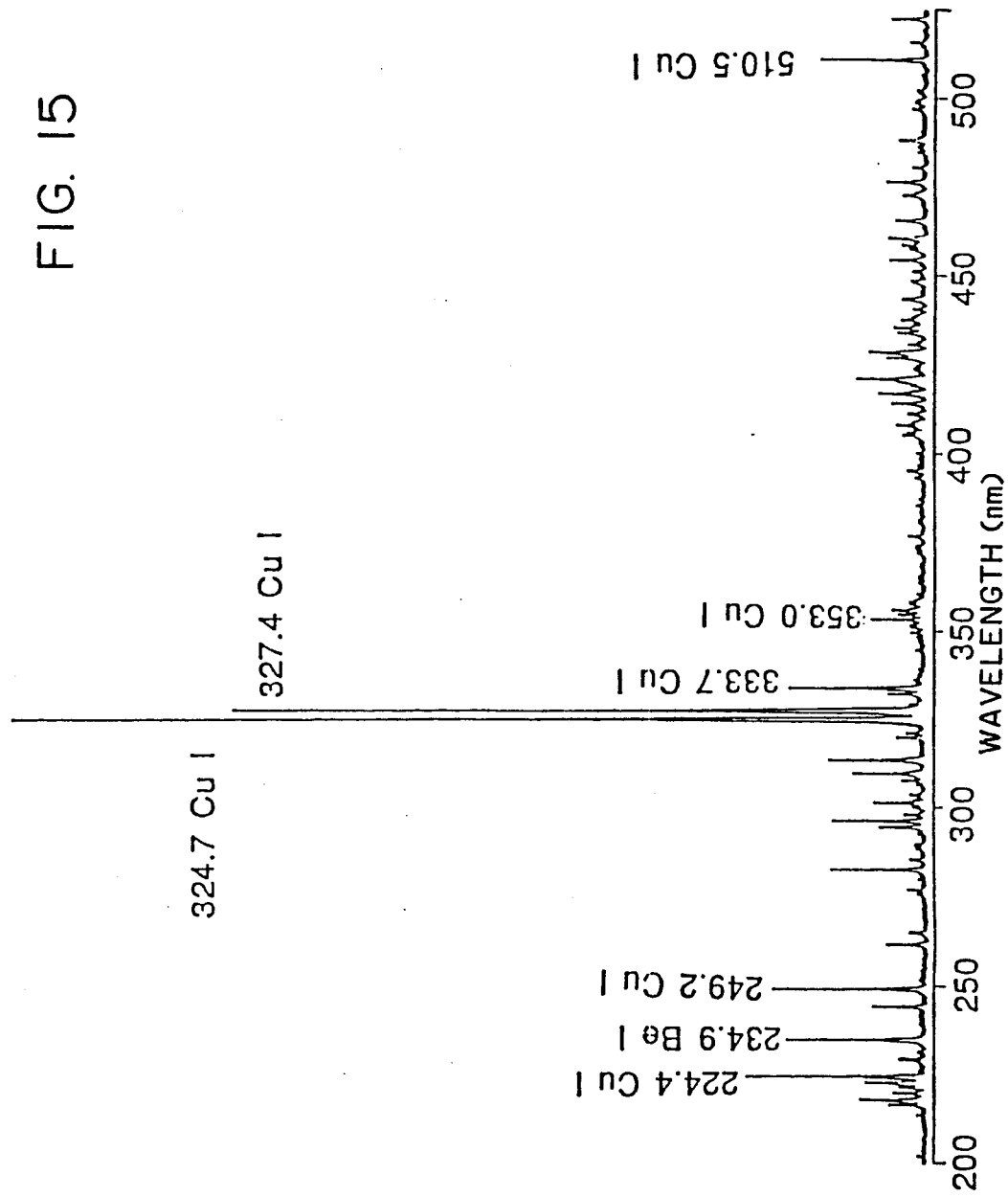
FIG. 15 is a radio frequency glow discharge atomic emission spectrum of a copper-beryllium alloy generated in accordance with the present invention.

The application of the glow discharge ion source of the present invention to the analysis of materials by atomic emission is demonstrated in FIG. 15. FIG. 15 is the emission spectrum of the NBS C1122 copper-beryllium alloy (analyzed by mass spectrometry in Example 1) under discharge conditions of 0.9 torr argon pressure and 15 watts RF power using the sample holder of FIG. 3.

Figure 16:
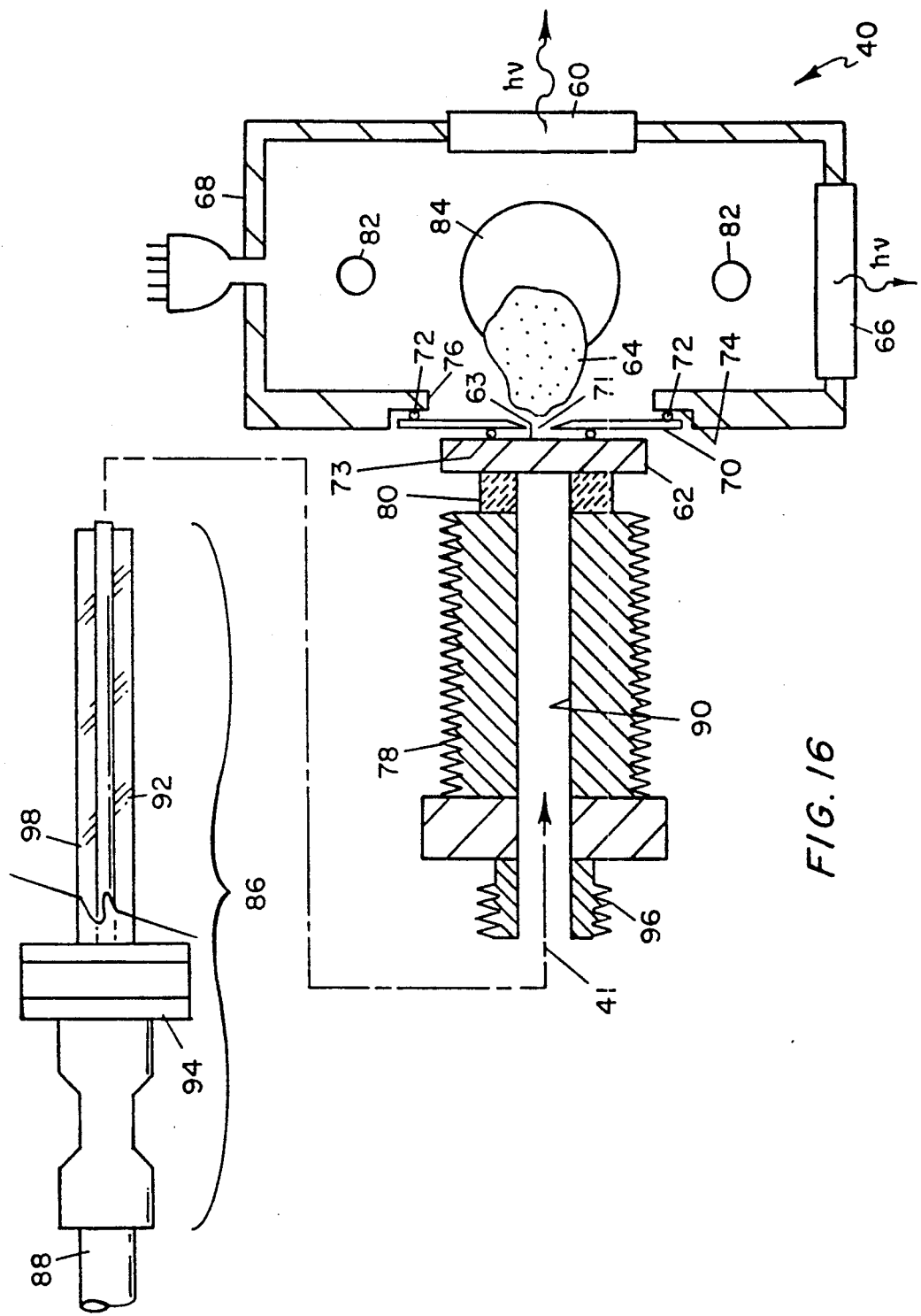
FIG. 16 is a schematic representation of an embodiment of a radio frequency powered glow discharge atomization/excitation source using an external sample mount geometry in accordance with the present invention.

In a further embodiment of an apparatus according to the present invention, a glow discharge atomization/excitation source incorporating an external sample mount geometry, is illustrated schematically in FIG. 16 and designated generally by the numeral 40. The apparatus includes an enclosure that defines a vacuum chamber. The walls of the enclosure, which is shown in FIG. 16 in a rectangular shape but may take other shapes, are desirably formed of a stainless steel body 68. The stainless steel walls forming the interior surface of the vacuum chamber define an electrode surface area exposed to the interior of the vacuum chamber and can be electrically connected to ground 120, as shown schematically in FIG. 17 for example.

The enclosure further defines a sample port that communicates between the interior and the exterior of the vacuum chamber. As embodied herein and shown schematically in FIG. 16 for example, the sample port is an opening 76 defined in chamber body 68.

In further accordance with the apparatus of the present invention, the enclosure defines an external mount for receiving a solid sample external to the vacuum chamber. As embodied herein and shown schematically in FIG. 16 for example, the external mount can include a lip flange surface 74, which generally is defined in stainless steel body 68 and is oriented to face away from the interior of the chamber. Lip flange surface 74 forms part of the exterior surface of the chamber and frames sample port opening 76. Since lip flange surface 74 is defined in stainless steel body 68, the external mount is electrically connected to the stainless steel walls defining the electrode surface area exposed to the interior of the vacuum chamber.

As embodied herein and shown schematically in FIG. 16 for example, the external mount can include an external mounting plate in the form of an orifice disk 70. The external mounting plate is electrically connected, as by metal screws for example, to enclosure body 68. Moreover, the external mounting plate defines a sample hole in the form of an orifice 71 that is circumscribed by sample port 76 and so controls the exposure of surface 63 of sample 62 to negative glow 64. Orifice 71 defined in orifice disk 70 desirably can have a circular shape with a diameter on the order of about two to twelve millimeters. An orifice of 2 mm provides a higher power density, which is desirable to enhance emission intensity. At some point, the orifice becomes too small to be able to accommodate dark spaces. With a 2 mm diameter orifice, a chamber pressure of from about 4 or 5 torr and above, must be maintained. Otherwise, a dark space cannot fit inside the orifice, and consequently no discharge will occur.

A conformable mounting plate sealing gasket in the form of an O-ring 72 is desirably disposed between the interior surface of the periphery of orifice disk 70 and lip flange surface 74 formed around sample port opening 76. The central opening defined in O-ring 72 is large enough to surround sample port opening 76. Moreover, the O-ring gasket is able to conform its shape sufficiently under the application of pressure so that a vacuum tight seal is formed between the mounting plate and the exterior of the vacuum chamber enclosure. O-ring 72 is desirably formed of a rubber soft enough to ensure an excellent seal under vacuum conditions.

In yet further accordance with the apparatus of the present invention, a torque bolt can be provided to bias and secure the sample so as to expose a surface of the sample to the interior of the vacuum chamber. As embodied herein and shown schematically in FIG. 16 for example, a brass torque bolt 78 is disposed outside the vacuum chamber defined by the enclosure. In order to electrically insulate the brass bolt from the sample, a ceramic spacer 80 is desirably disposed between the bolt and the sample 62.

In still further accordance with the present invention, means are provided to furnish a vacuum tight seal and maintain a less than one dark space separation between the surface forming the vacuum chamber electrode and a surface of the sample exposed to the interior of the vacuum chamber when the sample is secured to the external mount of the enclosure. As embodied herein and shown in FIG. 16 for example, a conformable sample sealing gasket in the form of an O-ring 73 is configured so as to be disposable against and between a first surface and a second surface so as to provide a vacuum tight seal and maintain a less than one dark space separation between the first surface and the second surface when the torque bolt secures the sample against the sample sealing gasket. Desirably, O-ring 73 is disposed between the exterior surface of orifice disk 70 and surface 63 of sample 62. Accordingly, a separation distance of less than one dark space is maintained between the first surface, which is the sample's surface 63 facing toward the interior of the vacuum chamber, and the second surface, which is the mounting plate surface facing away from the interior of the vacuum chamber, when torque bolt 78 secures sample 62 against sample sealing gasket 73. A suitable gasket for O-ring 73 is formed of TEFLON TM for example because of higher heat resistant properties of this material than rubber. Pressure is applied to form a vacuum-tight seal between sample 62 and orifice disk 70 and between orifice disk 70 and lip 74 of chamber body 68 by rotation of threaded brass torque bolt 78 against the insulating compression ring formed as spacer 80. Insulating spacer 80 also functions to prevent bolt 78 from damaging the sample when the bolt is tightened to secure the sample to the external mount.

In some embodiments of the sample securing and dark space maintaining means, the mounting plate, such as orifice disk 70, can be formed as a unitary part of enclosure body 68. However, such embodiments would forego the advantages of the interchangeability of mounting plates with differently sized and/or shaped orifices.

Figure 18B:
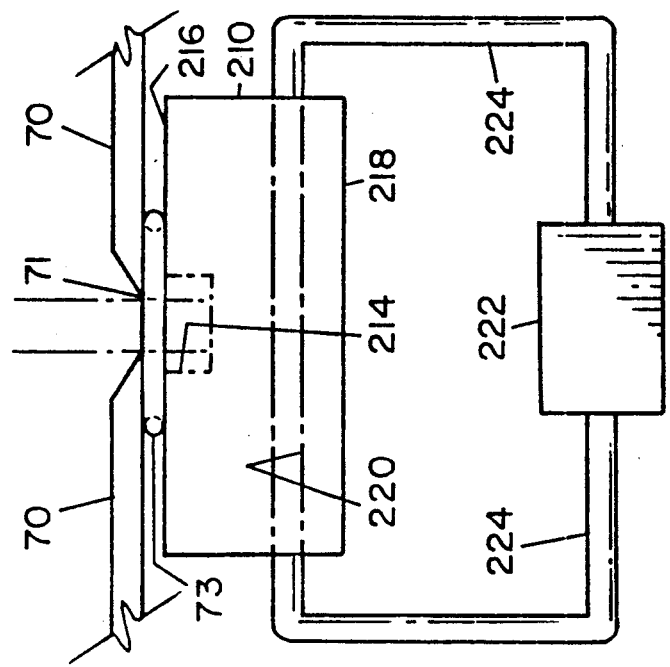
FIG. 18(b) is a schematic illustration of a side view of embodiments of components of an embodiment of the apparatus of the present invention.
Figure 18A:
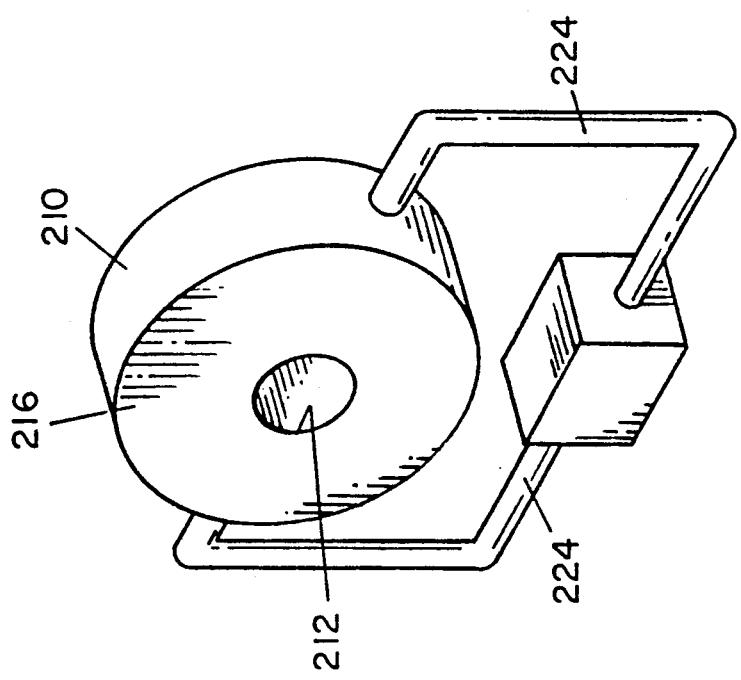
FIG. 18(a) schematically illustrates an embodiment of an elevated perspective view of a component of an embodiment of the apparatus of the present invention.

In still other embodiments of the sample securing and dark space maintaining means, a sample holder is provided in the form of a mold. Some samples are provided in a powdered form, and testing of such samples requires a mold in which the powdered sample material can be compacted and held. As shown in FIGS. 18(a) and (b) for example, the sample securing and dark space maintaining means can include a holder 210, which can be formed of an electrically conducting material such as copper for example. Holder 210 defines a recess 212 having side walls 214 (shown in phantom in FIG. 18(b)) spaced apart from one another over an area larger than the area of the sample hole 71 in the mounting plate 70, or the sample port defined in the enclosure if the mounting plate is part of a unitary structure including the chamber body. The compacted powdered sample material is received in the recess 212, which typically is about 2 mm deep and about one half inch in diameter for a circular disk-shaped holder 210 of 2 inch diameter. As shown in FIG. 18(b) for example, the one-half inch breadth of recess 212 is smaller than the open diameter of O-ring 73, which must surround recess 212 to provide the requisite vacuum seal against holder surface 216, which is disposed to face the interior of the vacuum chamber. The sample material typically will fill the recess up to the level of the surface 216. The opposite surface 218 of holder 210 will be electrically connected to the RF power source. Desirably, the breadth of the orifice 71 is smaller than the breadth of the recess. In this way, only the compacted surface of the sample material becomes exposed to the glow discharge, and no portion of the holder becomes exposed to the glow discharge. Accordingly, the holder 210 is not sputtered during the glow discharge phenomenon. Moreover, the holder preferably will be formed of a material such as metal which is strong enough to withstand the pressure applied by torque bolt 78 needed to secure the holder to the external mount via an O-ring 73 or other gasket separation that produces the less than one dark space distance between the surface of the compacted sample material and the external mount electrically connected to ground along with the remainder of the enclosure electrode.

In an RF glow discharge source such as the present invention, the dark space for any given sample material should fall within the range of from about 0.5 mm to about 4.0 mm. However, the dark space is inversely proportional to the power of the glow discharge and also inversely proportional to the pressure in the vacuum chamber during the glow discharge phenomenon. Thus, at a relatively high chamber pressure of about 10.0 torr, the dark space might be on the order of about 0.2 mm at a discharge power of about 10.0 watts. In addition, rotation of the torque bolt can result in more or less deformation of the sample sealing gasket, and such control over the extent of gasket deformation can serve to adjust the separation to less than one dark space while still maintaining the requisite vacuum seal.

Thus, the torque bolt, the insulating spacer, the conformable sample sealing gasket, the mounting plate, the mounting plate sealing gasket, and the lip flange surface cooperate to provide means for securing the sample to the external mount wherein at least a portion of the sample forms a vacuum seal around the sample opening defined in the vacuum chamber and maintains less than one dark space separation from the counterelectrode defined by the enclosure. (Because the electrode defined by the enclosure is maintained at the opposite electrical polarity to the electrical polarity of the sample, the enclosure electrode is sometimes referred to as the counterelectrode.) The absence of any structures between the counterelectrode and the sample prevents the sputtering of any such intervening structures that might otherwise cause adulteration of the sputtered sample material and the uncertainties and complexities attendant such adulteration. Moreover, the mechanism securing the sample remains outside the vacuum chamber, and this prevents material from the securing mechanism from being sputtered and complicating the analysis of the sample. Additionally, the external mount geometry of the apparatus of the present invention can readily accommodate a sample of almost any size or shape. The only dimensional requirement demanded of the sample is that the relevant portion of surface 63 of sample 62 must be sufficiently uniform, allowing for the ability of O-ring 73 to conform sufficiently to irregular shapes and still form a vacuum seal, so that a vacuum seal can be formed when surface 63 is pressed against O-ring 73. Furthermore, unusually shaped samples can be accommodated by the provision of an orifice disk 70 configured with a surface topography appropriate to ensure the requisite vacuum tight seal. In addition, orifice disk 70 can be replaced with another orifice disk having a differently sized or shaped orifice, if desired. For example, instead of a circular shape, orifice 71 can take the shape of an elongated slot having a uniform width along its entire length.

In still further accordance with the apparatus of the present invention, means are provided for applying a radio frequency electromagnetic potential between the counterelectrode, which is exposed to the interior of the vacuum chamber, and the sample to be received by the external mount. As embodied herein and shown schematically in FIG. 16 for example, an RF feedthrough 86 can be electrically attached to the end of a coaxial RF power cable (RG 213/U) 88, which can be inserted into an elongated cavity 90 defined longitudinally through bolt 78 and spacer 80. For example, one end of power cable 88 can be connected to an elongated copper conductor rod 92 via a male type-N coaxial connector 94, wherein conductor rod 92 can be configured with a circular transverse cross-sectional diameter of 3.2 millimeters. A female coaxial connector 96 can be defined at the end of bolt 78 opposite the end of bolt 78 disposed to press against spacer 80. When male connector 94 is mated to female coaxial connector 96, the free end of conductor rod 92 makes contact with the back of sample 62. A circular cylindrical annular glass insulator member 98 can serve as an electrically insulating sheath that surrounds conductor 92 and effectively prevents arcing between conductor 92 and bolt 78.

Figure 17:
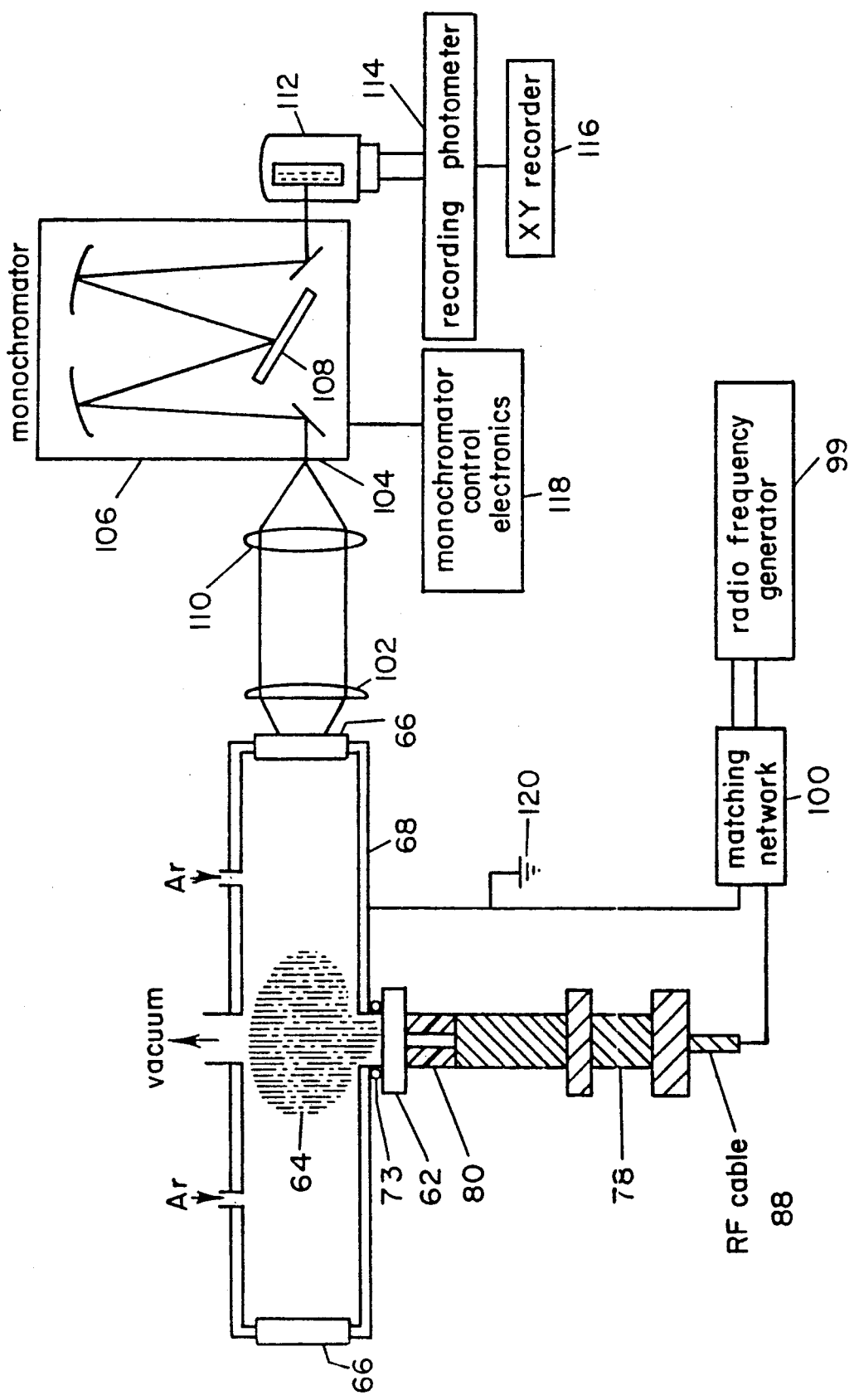
FIG. 17 is a schematic representation in accordance with the present invention of an embodiment of instrumentation for radio frequency powered glow discharge atomic emission spectrometry using an external sample mount geometry source of the type shown in FIG. 16.

Although no distinctly defined ground exists in the RF discharge apparatus of the present invention, sample 62 is often referred to as the cathode by analogy to the dc discharge apparatus. This convention is used in the present description. As shown in FIG. 17 for example, chamber body 68 acts as an anode and is connected to ground 120. Chamber body 68 serves as the larger counterelectrode, and sample 62 serves as the smaller electrode. A counterelectrode to electrode surface area ratio of about 500 has been found to be effective, and with a ratio of this magnitude, substantially all of the bias voltage should reside on sample 62.

As shown in FIG. 17 for example, an RF generator 99 and a matching network 100 are electrically connected to RF power cable 88. A suitable RF generator and matching network are a model RF5S and a model AM-5, respectively, available from RF Plasma Products, Inc., of Marlton, N.J. A driving potential provided by RF generator 98 desirably is sinusoidally modulated at 13.56 megahertz. RF generator 99 can supply power over a range of from zero to 100 watts. The optimum power for any given sample, depends in large measure on the type of material forming the sample. A matching network 100 employs a capacitive coupling in which a blocking capacitor is connected in series with the RF generator 99 to prevent any net current from flowing through the electrode circuit. It should be noted that if the discharge is directly coupled (i.e., no blocking capacitor is interposed between the sample and one of the presently available RF generators), bias potentials are not allowed to develop, since they are continuously compensated by electron flow through the electrode circuit. Thus, the capacitive matching network connected in series between the cathode and the RF power supply is essential when using one of the presently available RF power sources to generate the glow discharge.

The dc self-bias potential is directly (and approximately linearly) related to RF generator output power and inversely related to the discharge pressure within the discharge chamber. It appears that current is the dominant avenue for increasing discharge power. Moreover, operation at high pressure might be preferable from an analytical standpoint. The extent of excitation, as measured by excitation temperature measurements, should generally increase with RF power and decrease with increasing chamber pressure. The sputter rate in the RF discharge increases with chamber pressure at a constant RF power, and this probably is a result of an associated discharge current increase. The sputter rate increases with RF power for any given chamber pressure. Conditions of high pressure in the range of 6 to 10 torr and high RF power appeared to provide attractive emission intensities of sputtered species. Such conditions represent an effective trade-off between atomization rate and the extent of excitation.

The use of the discharge chamber walls, rather than the sample, as the "powered" electrode, may improve the efficiency of the coupling of the RF power to the discharge, as well as help avoid any coupling differences from sample-to-sample. Additionally, the size of the sampling orifice may have an effect on analytical characteristics such that an optimum diameter for the orifice might exist.

Cooling of the discharge chamber and sample also could be advantageous, owing to the associated reduction of water vapor in the discharge. In embodiments employing a holder, such as for powdered sample materials, provision can be made in conjunction with the holder so that the holder can be cooled, and such cooling can keep the sample cooled by conduction heat transfer. Such cooling means are disclosed for example in Hall et al. U.S. Pat. No. 4,853,539, the disclosure of which is hereby incorporated herein by reference. As schematically shown in FIG. 18(b) for example, a coolant is circulated, as by a pump, through a coolant channel 220 (shown in phantom by the dashed lines) provided through holder 210 and connected to a coolant supply 222 via conduits 224, coolant supply 222 also including means for circulating the coolant such as a pump.

In yet further accordance with the present invention, the RF frequency is modulated so as to provide the power to the sample in pulses which have a frequency of anywhere from 1 to 1,000 Hertz. The length of each pulse can be anywhere from about 1 millisecond to about one-half second. By pulsing the power provided to the sample, the glow discharge is in effect turned on and off between very low powers to very high powers. This permits the sample to cool off between power pulses. The use of these short bursts of power permit the application of higher powers during the power bursts than otherwise would be possible if the power were provided at the steady state rate of the RF power source. Moreover, the glow discharge can be operated at higher overall average powers than is the case without pulsing the discharge. Furthermore, the pulsed discharge at the higher powers can be synchronized with the analyzing instrumentation so that the detection of the analyzing instrumentation only occurs at the optimum time relative to the occurrence of the short pulse of high power. The synchronous optimum timing may vary depending upon the type of analysis being performed. This so-called synchronous detection process improves the quality of the data that can be gathered by the analyzing instrumentation.

The vacuum chamber enclosure defines at least one output port connectable to means for analyzing the contents of the vacuum chamber. In some embodiments, each output port can include an optical window. As shown schematically in FIG. 16 for example, the walls of the enclosure defining the vacuum chamber can include one or more optical windows. In the embodiment shown in FIG. 16, two optical windows are provided. A fused silica window 60 is mounted directly opposite sample 62, such that both the discharge glow 64 and the sample surface 63 may be viewed simultaneously. A second fused silica window 66 is defined as part of the side of chamber body 68 adjacent to the side of chamber 68 onto which sample 62 is mounted. Window 66 is oriented for the purpose of allowing optical monitoring of negative glow 64 while avoiding noise which might otherwise originate from surface 63 of sample 62. The optical geometry which includes a window 60 mounted directly opposite the sample 62 is known as the "glow+cathode" geometry. The optical geometry using a window 66 mounted perpendicular to the sample axis (indicated by arrow 41) is known as the "glow only" geometry. Moreover, the dual window design, such as shown in FIG. 16, facilitates direct comparison of analyte emission intensities, signal-to-noise ratios, and emission spectra obtained with each of the two optical geometries. The wavy stem arrows designated hv in FIG. 16 are intended to represent electromagnetic wave energy emitted through window 60 or 66 for analysis by further analyzing instrumentation.

When the RF glow discharge of the present invention is to be used to conduct atomic absorption analyses, the optical geometry should include at least two windows disposed as in the "glow only" geometry. The two windows should be disposed in direct line of sight of one another and to opposite sides of the glow discharge. As embodied herein and shown in FIG. 17 for example, a vacuum chamber 68 includes a pair of oppositely disposed output ports in the form of windows 66 disposed on opposite sides of glow discharge 64. Each window 66 is in a direct line of sight of the other window 66, but shielded from a line of sight which would encompass sample 62.

In some other embodiments, each output port can include or be connectable to an intermediate vacuum lock where ions or other sputtered species may be collected for further transmission to an analyzing instrument such as a mass spectrometer for example. This type of arrangement is illustrated schematically in FIG. 5 where one of the ports of the six way cross is connected to an intermediate vacuum region 30 and an analyzing region 32 of a mass spectrometer.

Excitation temperatures for the RF discharge source, particularly in the glow plus cathode mode, are significantly higher, and this fact demonstrates the great potential of the RF glow discharge sources for the emission detection of sputtered species, including elements that possess high-lying resonance states. Signal-to-noise ratios obtained from the glow only and glow plus cathode optical geometries appear statistically equal, while emission intensities of the glow plus cathode optical geometry are two to five times higher than the intensities obtained using the glow only optical geometry. Since much of the noise associated with the emission measurements may originate from the sample surface itself, higher signal-to-noise ratios may be obtainable with the glow only optical configuration. However, because of the much lower emission intensities obtained with the glow only configuration, the glow plus cathode geometry might be more analytically attractive.

The enclosure defines at least one gas inlet port connectable to means for supplying gas into the vacuum chamber. As shown schematically in FIG. 16 for example, an inert gas such as argon enters the discharge chamber defined by chamber body 68 through one or both of two 0.63 cm diameter circular compression fittings 82 defining gas inlet ports for the introduction of the inert gas. Inlet ports 82 are mounted on the top of the chamber and disposed equidistant from sampling orifice 71 in orifice disk 70.

The enclosure defines a vacuum port connectable to means for evacuating the vacuum chamber. As shown schematically in FIG. 16 for example, defined in the top of the chamber is a vacuum port 84 which leads to an adjustable-flow (bellows) vacuum valve (not shown) that controls the degree of vacuum present within the discharge chamber defined by chamber body 68. The support gas flow rate of the inert gas introduced through ports 82 for any given pressure within the chamber may be manipulated by simultaneous adjustment of the vacuum valve and gas line needle valve (not shown) controlling the introduction of the inert gas. The range of pressures suitable for maintaining the RF glow discharge phenomenon are from about 0.1 to 10 torr.

The use of the external mount geometry RF glow discharge atomization/excitation source of the present invention in connection with atomic emission spectrometry is illustrated schematically in FIG. 17 for example. Photons emitted from negative glow 64 are collected by means of a plano-convex lens 102 and focused via a focusing lens 110 onto the entrance slit 104 of a 240 millimeter focal length Czerney Turner mount monochromator 106 equipped with a 2400 g/mm holographic grating 108. Such monochromator is available from CVI Laser Corp. of Albuquerque, N.M. under the tradename Digikrom 240 TM. A photomultiplier tube 112 such as an RCA 1P28 TM is powered by a dc voltage regulated power supply (not shown) and is employed as a transducer. Photocurrent exiting the photomultiplier tube 112 is fed into a digital picoammeter 114 (model 480 TM available from Keithley Instruments, Inc., of Cleveland, Ohio) such that emission intensities may be recorded manually. Emission spectra are obtained via an XY recorder 116 (model 200 TM, Houston Instruments, of Austin, Tex.) connected to the output of picoammeter 114. The external mount geometry RF glow discharge atomization/excitation source is desirably mounted on an XYΦ optical mount (not shown) so that the two different optical geometries can be easily interconverted by rotation of the mount relative to the optical equipment such as monochromator 106, which is controlled by monochromator control electronics 118.

What is claimed is:

1. An apparatus for using radio frequency electromagnetic energy to sustain a glow discharge atomization/excitation source in the presence of a solid sample, whether the sample is electrically conducting or nonconducting, the glow discharge atomization/excitation source being suitable for atomic emission analyses, or atomic absorption analyses, or atomic mass spectrometry analyses, the apparatus comprising:
   (a) an enclosure,
      i) said enclosure defining a vacuum chamber,
      ii) said enclosure defining a vacuum port connectable to means for evacuating said vacuum chamber,
      iii) said enclosure defining at least one gas inlet port connectable to means for supplying gas into said vacuum chamber,
      iv) said enclosure defining an output port connectable to means for analyzing the contents of said vacuum chamber,
      v) said enclosure defining an external mount for receiving a solid sample external to said vacuum chamber,
      vi) said external mount defining a sample opening for communicating between said vacuum chamber and the sample to be received by said external mount,
      vii) said enclosure defining an electrode having a surface exposed to the interior of said vacuum chamber, and
      viii) said electrode being electrically connected to said external mount so as to be maintained at the same electrical potential as said external mount;
   (b) means for securing the sample to said external mount wherein at least a portion of the sample forms a vacuum seal around said sample opening; and
   (c) means for applying a radio frequency electromagnetic potential between said electrode and the sample to be received by said external mount.

2. An apparatus as in claim 1, wherein:
said output port is oriented so as to maximize the signal-to-noise ratio for the analyzing means to be connected to the apparatus to analyze the signal received from the contents of the vacuum chamber during operation of the apparatus.

3. An apparatus as in claim 1, wherein:
said output port defines a window through which electromagnetic radiation can be transmitted from with said vacuum chamber during operation of the apparatus.

4. An apparatus as in claim 3, wherein:
said window is formed of fused silica.

5. An apparatus as in claim 1, wherein:

i) said electrode surface area exposed to said vacuum chamber is larger than the area of said sample opening, and ii) said electrode is electrically connectable to ground.

6. An apparatus as in claim 1, wherein:

said external mount for receiving a solid sample external to said vacuum chamber includes:

i) a mounting surface, ii) said mounting surface being defined in said enclosure and disposed to adjoin a portion of said enclosure which defines said sample opening, iii) said mounting surface defining a portion of the exterior surface of said enclosure outside of said vacuum chamber, iv) a mounting plate, v) said mounting plate defining a sample hole therethrough, vi) a conformable mounting plate sealing gasket, vii) said mounting plate sealing gasket being configured with an opening large enough to surround said sample opening, and viii) said mounting plate sealing gasket being disposed against and between said enclosure mounting surface and said mounting plate and configured so as to provide a vacuum tight seal.

7. A method as in claim 1, wherein: said step of disposing a first surface of the sample so that a portion of the surface's area becomes exposed to the interior of the chamber includes the step of ensuring that the area of said first sample surface is less than the area of the electrode exposed to the interior of the chamber.

8. An apparatus for using radio frequency electromagnetic energy to sustain a glow discharge atomization/excitation source in the presence of a solid sample, whether the sample is electrically conducting or nonconducting, the glow discharge atomization/excitation source being suitable for atomic emission analyses, or atomic absorption analyses, or atomic mass spectrometry analyses, the apparatus comprising:

(a) an enclosure, i) said enclosure defining a vacuum chamber, ii) said enclosure defining a vacuum port connectable to means for evacuating said vacuum chamber, iii) said enclosure defining at least one gas inlet portion connectable to means for supplying gas into said vacuum chamber, iv) said enclosure defining an output port connectable to means for analyzing the contents of said vacuum chamber, v) said enclosure defining an external mount for receiving a solid sample external to said vacuum chamber, vi) said external mount defining a sample opening for communicating between said vacuum chamber and the sample to be received by said external mount, vii) said enclosure defining an electrode having a surface exposed to the interior of said vacuum chamber, and viii) said electrode being electrically connected to said external mount;

(b) means for securing the sample to said external mount wherein at least a portion of the sample forms a vacuum seal around said sample opening; and (c) means for applying a radio frequency electromagnetic potential between said electrode and the sample to be received by said external mount, wherein:

said means for securing the sample to said external mount wherein at least a portion of the sample forms a vacuum seal around said sample opening comprises:

i) a conformable sample sealing gasket, ii) a torque bolt disposed outside said vacuum chamber so as to be able to bias and secure the sample against said sample sealing gasket, iii) said sample sealing gasket being configured so as to be disposable against and between a first surface and a second surface so as to provide a vacuum tight seal and maintain a less than one dark space separation between said first surface and said second surface when said torque bolt secures the sample against said sample sealing gasket, iv) said first surface being a surface of the sample to be received by said external mount, and v) said second surface being a sample mount surface located exterior to said vacuum chamber and surrounding said sample opening of said external mount.

9. An apparatus for using radio frequency electromagnetic energy to sustain a glow discharge atomization/excitation source in the presence of a solid sample, whether the sample is electrically conducting or nonconducting, the glow discharge atomization/excitation source being suitable for atomic emission analyses, or atomic absorption analyses, or atomic mass spectrometry analyses, the apparatus comprising:

(a) an enclosure, i) said enclosure defining a vacuum chamber, ii) said enclosure defining a vacuum port connectable to means for evacuating said vacuum chamber, iii) said enclosure defining at least one gas inlet port connectable to means for supplying gas into said vacuum chamber, iv) said enclosure defining an output port connectable to means for analyzing the contents of said vacuum chamber, v) said enclosure defining an external mount for receiving a solid sample external to said vacuum chamber, vi) said external mount defining a sample opening for communicating between said vacuum chamber and the sample to be received by said external mount, vii) said enclosure defining an electrode having a surface exposed to the interior of said vacuum chamber, and viii) said electrode being electrically connected to said external mount;

(b) means for securing the sample to said external mount wherein at least a portion of the sample forms a vacuum seal around said sample opening; and (c) means for applying a radio frequency electromagnetic potential between said electrode and the sample to be received by said external mount, wherein:

said external mount is disposed so as to be less than one dark space from the sample when the sample is disposed in said securing means and wherein said securing means is disposed so as to be shielded from the glow discharge when the sample is disposed in said securing means and said electromagnetic application means is applying an electromagnetic potential between the sample and said external mount.

10. An apparatus for using radio frequency electromagnetic energy to sustain a glow discharge atomization/excitation source in the presence of a solid sample, whether the sample is electrically conducting or nonconducting, the glow discharge atomization/excitation source being suitable for atomic emission analyses, or atomic absorption analyses, or atomic mass spectrometry analyses, the apparatus comprising:
(a) an enclosure,
  i) said enclosure defining a vacuum chamber,
  ii) said enclosure defining a vacuum port connectable to means for evacuating said vacuum chamber,
  iii) said enclosure defining at least one gas inlet port connectable to means for supplying gas into said vacuum chamber,
  iv) said enclosure defining an output port connectable to means for analyzing the contents of said vacuum chamber,
  v) said enclosure defining an external mount for receiving a solid sample external to said vacuum chamber,
  vi) said external mount defining a sample opening for communicating between said vacuum chamber and the sample to be received by said external mount,
  vii) said enclosure defining an electrode having a surface exposed to the interior of said vacuum chamber, said electrode surface area exposed to the interior of said vacuum chamber being larger than the area of said sample opening, said electrode being electrically connectable to ground; and
  viii) said electrode being electrically connected to said external mount;
(b) means for securing the sample to said external mount wherein at least a portion of the sample forms a vacuum seal around said sample opening; and
(c) means for applying a radio frequency electromagnetic potential between said electrode and the sample to be received by said external mount, wherein:
said means for applying a radio frequency electromagnetic potential between said electrode and the sample to be received by said external mount comprises:
  i) a radio frequency coaxial cable,
  ii) a first coaxial connector connected to one end of said RF coaxial cable,
  iii) an elongated conductor having a first end and a second end disposed opposite said first end,
  iv) said first end of said conductor being connected to said first coaxial connector,
  v) a second coaxial connector disposed so that upon engaging said first coaxial connector said second end of said conductor electrically engages the sample during operation of the apparatus, and
  vi) an electrically insulating sheath surrounding said conductor between said first and second ends of said conductor.

11. An apparatus as in claim 10, further comprising:
(d) a radio frequency generator; and
(e) a matching network,
  i) said matching network being electrically connected to said radio frequency generator,
  ii) said matching network being electrically connected to said radio frequency coaxial cable, and
  iii) said matching network being electrically connected to said electrode.

12. An apparatus as in claim 11, wherein:
i) said matching network includes a capacitive impedance.

13. An apparatus as in claim 12, wherein:
i) said matching network is electrically connected in series between said conductor and said radio frequency generator.

14. An apparatus for using radio frequency electromagnetic energy to sustain a glow discharge atomization/excitation source in the presence of a solid sample, whether the sample is electrically conducting or nonconducting, the glow discharge atomization/excitation source being suitable to atomic emission analyses, or atomic absorption analyses, or atomic mass spectrometry analyses, the apparatus comprising:
(a) an enclosure,
  i) said enclosure defining a vacuum chamber,
  ii) said enclosure defining a vacuum port connectable to means for evacuating said vacuum chamber,
  iii) said enclosure defining at least one gas inlet port connectable to means for supplying gas into said vacuum chamber,
  iv) said enclosure defining an output port connectable to means for analyzing the contents of said vacuum chamber,
  v) said enclosure defining an external mount for receiving a solid sample external to said vacuum chamber,
  vi) said external mount defining a sample opening for communicating between said vacuum chamber and the sample to be received by said external mount,
  vii) said enclosure defining an electrode having a surface exposed to the interior of said vacuum chamber, and
  viii) said electrode being electrically connected to said external mount;
(b) means for securing the sample to said external mount wherein at least a portion of the sample forms a vacuum seal around said sample opening; and
(c) means for applying a radio frequency electromagnetic potential between said electrode and the sample to be received by said external mount, wherein:
said external mount for receiving a solid sample external to said vacuum chamber includes:
  i) a mounting surface,
  ii) said mounting surface being defined in said enclosure and disposed to adjoin a portion of said enclosure which defines said sample opening,
  iii) said mounting surface defining a portion of the exterior surface of said enclosure outside of said vacuum chamber,
  iv) a mounting plate,
  v) said mounting plate defining a sample hole therethrough,
  vi) a conformable mounting plate sealing gasket,
  vii) said mounting plate sealing gasket being configured with an opening large enough to surround said sample opening, and viii) said mounting plate sealing gasket being disposed against and between said enclosure mounting surface and said mounting plate and configured so as to provide a vacuum tight seal, said means for securing the sample to said external mount wherein at least a portion of the sample forms a vacuum seal around said sample opening comprising:
  i) a conformable sample sealing gasket,
  ii) a torque bolt disposed outside said vacuum chamber so as to be able to bias and secure the sample against said sample sealing gasket,
  iii) said sample sealing gasket being configured with an opening large enough to surround said sample hole of said mounting plate,
  iv) said sample sealing gasket being configured so as to be disposable against and between a first surface and a second surface so as to provide a vacuum tight seal and maintain a less than one dark space separation between said first surface and said second surface when said torque bolt secures the sample against said sample sealing gasket,
  v) said first surface being a surface of the sample to be received by said external mount, and
  vi) said second surface being a mounting plate surface located exterior to said vacuum chamber and surrounding said sample hole of said mounting plate.

15. An apparatus as in claim 14, wherein:
  i) said electrode surface area exposed to said vacuum chamber is larger than the area of said sample hole defined in said mounting plate, and
  ii) said electrode is electrically connectable to ground.

16. An apparatus as in claim 15, wherein:
said means for applying a radio frequency electromagnetic potential between said electrode and the sample to be received by said external mount comprises:
  i) a radio frequency coaxial cable,
  ii) a first coaxial connector connected to one end of said RF coaxial cable,
  iii) an elongated conductor having a first end and a second end disposed opposite said first end,
  iv) said first end of said conductor being connected to said first coaxial connector,
  v) a second coaxial connector configured and disposed so that when said second coaxial connector engages said first coaxial connector and the sample is secured to the external mount, then said second end of said conductor electrically engages the sample during operation of the apparatus, and
  vi) an electrically insulating sheath surrounding said conductor along the length of said conductor extending between said first and second ends of said conductor.

17. An apparatus as in claim 16, further comprising:
(d) a radio frequency generator; and
(e) a matching network,
  i) said matching network being electrically connected to said radio frequency generator,
  ii) said matching network being electrically connected to said radio frequency coaxial cable, and
  iii) said matching network being electrically connected to said electrode.

18. An apparatus as in claim 17, wherein:

i) said matching network includes a capacitive impedance.

19. An apparatus as in claim 18, wherein:
  i) said matching network is electrically connected in series between said conductor and said radio frequency generator.

20. An apparatus for using radio frequency electromagnetic energy to transform a solid sample, whether the sample is electrically conducting or nonconducting, into a glow discharge atomization/excitation source suitable for atomic emission analyses, or atomic absorption analyses, or atomic mass spectrometry analyses, the apparatus comprising:
(a) an enclosure,
  i) said enclosure defining a vacuum chamber,
  ii) said enclosure defining a vacuum port connectable to means for evacuating said vacuum chamber,
  iii) said enclosure defining at least one gas inlet port connectable to means for supplying gas into said vacuum chamber,
  iv) said enclosure defining an electrode having a surface exposed to said vacuum chamber,
  v) said electrode being electrically connectable to ground,
  vi) said enclosure defining an output port connectable to means for analyzing the contents of said vacuum chamber,
  vii) said enclosure defining a sample port communicating between the interior and the exterior of said vacuum chamber,
  viii) said enclosure defining a mounting surface,
  ix) said mounting surface defining a portion of the exterior surface of said enclosure outside of said vacuum chamber, and
  x) said mounting surface being disposed to adjoin a portion of said enclosure which defines said sample port;
(b) an external mounting plate,
  i) said external mounting plate defining a sample hole therethrough,
  ii) the area of said sample hole being smaller than said electrode surface area exposed to said vacuum chamber,
  iii) said external mounting plate being connected to said mounting surface so that said sample hole and said sample port are aligned, and
  iv) said external mounting plate being electrically connected to said electrode;
(c) a conformable mounting plate sealing gasket,
  i) said mounting plate sealing gasket being configured with an opening large enough to surround said sample port, and
  ii) said mounting plate sealing gasket being disposed against and between said enclosure mounting surface and said mounting plate and configured so as to provide a vacuum tight seal;
(d) a conformable sample sealing gasket;
(e) a torque bolt,
  i) said torque bolt being disposed outside said vacuum chamber so as to be able to bias and secure the sample against said sample sealing gasket,
  ii) said sample sealing gasket being configured so as to be disposable against and between a first surface and a second surface so as to provide a vacuum tight seal and maintain a less than one dark space separation between said first surface and said second surface when said torque bolt secures the sample against said sample sealing gasket, iii) said first surface being a surface of the sample to be mounted to said mounting plate, and iv) said second surface being an external surface of said mounting plate, said second surface being located exterior to said vacuum chamber and surrounding said sample hole of said external mounting plate;

(f) a radio frequency coaxial cable;

(g) a first coaxial connector connected to one end of said RF coaxial cable;

(h) an elongated conductor having a first end and a second end disposed opposite said first end, i) said first end of said conductor being connected to said first coaxial connector;

(i) a second coaxial connector, i) said second coaxial connector being disposed so that upon engaging said first coaxial connector said second end of said conductor electrically engages the sample during operation of the apparatus; and (j) an electrically insulating sheath surrounding said conductor between said first and second ends of said conductor.

21. A method of analyzing a sample of a material in solid form, comprising the steps of:

(a) introducing an inert gas into a low pressure chamber having an electrode exposed to the interior of the chamber;

(b) locating the sample outside the chamber;

(c) disposing a first surface of the sample so that a portion of the surface's area becomes exposed to the interior of the chamber;

(d) disposing said first surface of the sample less than one dark space from the electrode and without any conducting material between the sample and the electrode;

(e) initiating glow discharge within said chamber by applying a radio frequency potential between the sample and said electrode in the presence of an inert gas;

(f) maintaining said glow discharge in said chamber such that said inert gas is ionized and the ionized gas sputters said sample; and (g) analyzing said sputtered sample material.

22. A method as in claim 21, wherein: said step of applying a radio frequency potential between the sample and said electrode includes the step of electrically connecting said electrode to ground.

23. A method as defined in claim 22 wherein: the first surface of the sample is disposed by securing it so as to seal an opening defined in a wall which defines the chamber so that the desired low pressure can be maintained within the interior of the chamber.

24. Method as in claim 21, wherein: said step of disposing a first surface of the sample so that a portion of the surface's area becomes exposed to the interior of the chamber includes the step of ensuring that the area of said first sample surface is greater than the area of the electrode exposed to the interior of the chamber.

25. A method as in claim 24, wherein: said step of applying a radio frequency potential between the sample and said electrode includes the step of electrically connecting the sample to ground.

26. A method as set forth in claim 21, further comprising the step of:

(h) maintaining the glow discharge at a sufficiently low pressure so as to reduce redeposition of the sputtered sample material onto the first surface of the sample.

27. A method as set forth in claim 21, further comprising the step of:

(h) orienting the analyzing device relative to the first surface and to the glow discharge so as to maximize the signal-to-noise ratio of the signal being used to analyze the sputtered sample material.

28. A method as set forth in claim 21, further comprising the step of:

(h) orienting the analyzing device relative to the first surface and to the glow discharge so as to optimize the signal being used to analyze the sputtered sample material.

29. A method as set forth in claim 21, wherein: the step of analyzing said sputtered sample material includes subjecting the sputtered sample material to a mass spectrometric analysis, and the method further comprising the steps of:

(h) adjusting the pressure inside the chamber and the radio frequency power so as to orient the interface of the glow discharge and the dark space at the sampling cone of the analyzing device.

30. A method as in claim 21, wherein:

the radio frequency of the potential applied between the sample and the electrode is modulated.

31. A method as in claim 30, wherein:

the frequency of modulation is in the range of from 1 to 1,000 Hertz.

32. A method as in claim 30, wherein:

the length of each modulated pulse of RF potential is in the range of from about 1 millisecond to about one-half second.

33. A method as in claim 30, wherein:

the step of analyzing the sputtered sample material is conducted according to a synchronous detection process.

34. A method as in claim 21, wherein:

the step of locating the sample outside the chamber includes the step of compacting a powdered form of the sample into a mold that serves as the sample holder.

35. A method as in claim 34, wherein:

the holder is shielded from the glow discharge.

* * * * *

UNITED STATES PATENT AND TRADEMARK OFFICE
CERTIFICATE OF CORRECTION

PATENT NO. : 5,086,226
DATED : February 4, 1992
INVENTOR(S) : R. Kenneth Marcus It is certified that error appears in the above-identified patent and that said Letters Patent is hereby corrected as shown below:

Column 15, line 7, change "generator 98" to read --generator 99--.

Column 18, line 64, change "with" to read --within--.

Column 19, line 48, change "portion" to read --port--.

Column 22, line 19, change "to" to read --for--.

Column 23, line 8, change "comprising" to read --comprises--.

Column 25, line 56, change "Method" to read --A method--.

Signed and Sealed this

Tenth Day of August, 1993

Attest:

MICHAEL K. KIRK

*Attesting Officer*    *Acting Commissioner of Patents and Trademarks*

UNITED STATES PATENT AND TRADEMARK OFFICE
CERTIFICATE OF CORRECTION

PATENT NO. : 5,086,226
DATED : February 4, 1992
INVENTOR(S) : R. Kenneth Marcus

It is certified that error appears in the above-indentified patent and that said Letters Patent is hereby corrected as shown below:

Column 19, line 27, change "claim 1" to read --claim 22--.

Signed and Sealed this

Thirtieth Day of August, 1994

Attest:

BRUCE LEHMAN

*Attesting Officer*  *Commissioner of Patents and Trademarks*